(12) United States Patent
Hook et al.

(10) Patent No.: US 8,946,481 B2
(45) Date of Patent: Feb. 3, 2015

(54) PROCESS FOR PREPARING BIARYL SUBSTITUTED 4-AMINO BUTYRIC ACID OR DERIVATIVES THEREOF AND THEIR USE IN THE PRODUCTION OF NEP INHIBITORS

(71) Applicant: Novartis AG, Basel (CH)

(72) Inventors: David Hook, Rheinfelden (CH); Bernhard Wietfeld, Efringen-Kirchen (DE); Matthias Lotz, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/661,991

(22) Filed: Oct. 26, 2012

(65) Prior Publication Data

US 2013/0066101 A1    Mar. 14, 2013

Related U.S. Application Data

(63) Continuation of application No. 12/438,798, filed as application No. PCT/EP2007/007913 on Sep. 11, 2007, now abandoned.

(30) Foreign Application Priority Data

Sep. 13, 2006   (EP) .................................. 06120576

(51) Int. Cl.
*C07C 211/00* (2006.01)
*C07C 269/06* (2006.01)

(52) U.S. Cl.
CPC .................................. *C07C 269/06* (2013.01)
USPC .......................................................... 564/374

(58) Field of Classification Search
None
See application file for complete search history.

(56) References Cited

U.S. PATENT DOCUMENTS

| 5,217,996 | A | 6/1993 | Ksander | |
|---|---|---|---|---|
| 5,250,522 | A | 10/1993 | De Lombaert | |
| 5,550,119 | A | 8/1996 | De Lombaert | |
| 6,214,763 | B1 | 4/2001 | Dobbs et al. | 502/155 |
| 2004/0220049 | A1 | 11/2004 | Hems et al. | 502/150 |
| 2005/0101643 | A1 | 5/2005 | Blazecka et al. | 514/357 |

FOREIGN PATENT DOCUMENTS

| EP | 0673911 A1 | 9/1995 |
|---|---|---|
| WO | 0155090 A1 | 8/2001 |
| WO | 2004/085378 | 10/2004 |
| WO | 2006003196 A1 | 1/2006 |
| WO | 2005016178 A1 | 2/2006 |
| WO | 2006/057904 | 6/2006 |
| WO | 2006/069617 | 7/2006 |

OTHER PUBLICATIONS

Spindler et al. Tetrahedron: Asymmetry 15 (2004) 2299-2306.
Ksander, G.M. et al., "Dicarboxylic Acid Dipeptide Neutral Endopeptidase Inhibitors," J. Med. Chem., vol. 38, pp. 1689-1700 (1995).
Chi et al., 2005, "Rhodium-Catalyzed Asymmetric Hydrogenation", Modern Rhodium-Catalyzed Organic Reactions, pp. 1-31.

*Primary Examiner* — Clinton Brooks
(74) *Attorney, Agent, or Firm* — Matthew Mulkeen

(57) ABSTRACT

The invention relates to a process for producing a compound according to formula (i)

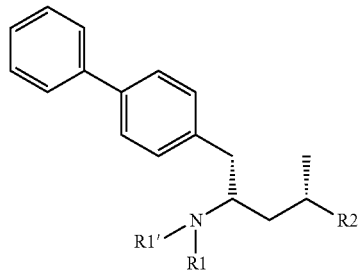

(i)

or salt thereof,
wherein R1 and R1' are independently hydrogen or an amine protecting group and R2 is a carboxyl group or an ester group, comprising reacting a compound according to formula (ii)

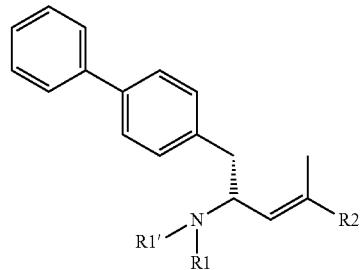

(ii)

or salt thereof,
wherein R1, R1' and R2 are defined as above, with hydrogen in the presence of a transition metal catalyst and a chiral ligand, wherein the transition metal is selected from group 7, 8 or 9 of the periodic table. Furthermore, the invention relates to products obtainable by said process and to their use in the production of NEP inhibitors. Moreover, the invention relates to the use of transition metal catalyst in the preparation of NEP inhibitors or prodrugs thereof.

28 Claims, 1 Drawing Sheet

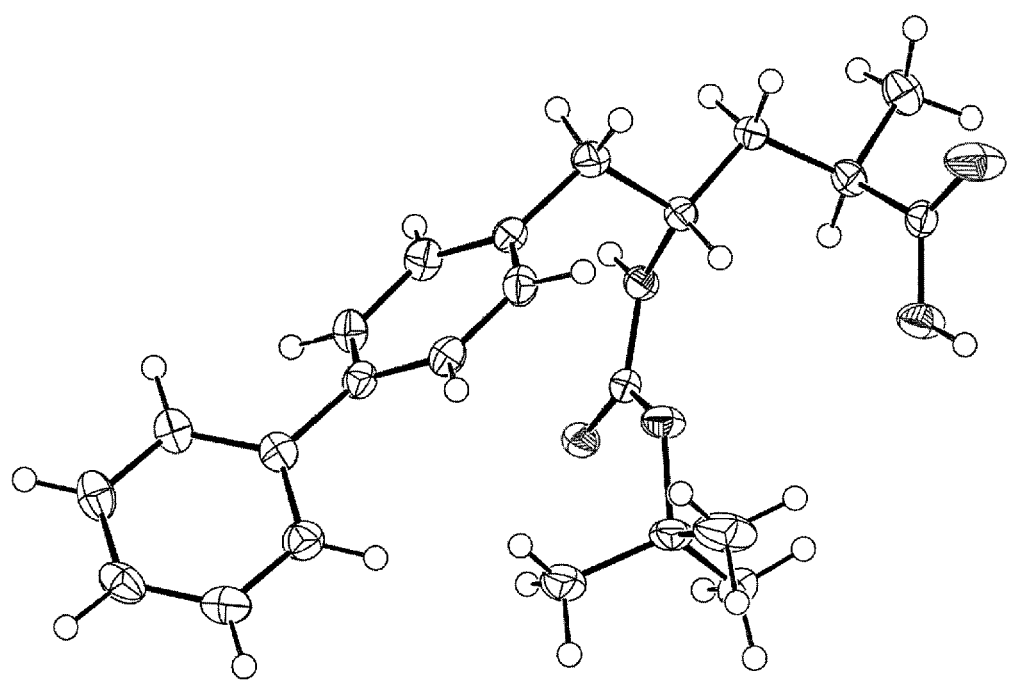

PROCESS FOR PREPARING BIARYL SUBSTITUTED 4-AMINO BUTYRIC ACID OR DERIVATIVES THEREOF AND THEIR USE IN THE PRODUCTION OF NEP INHIBITORS

The invention relates to a process for producing a compound according to formula (i),

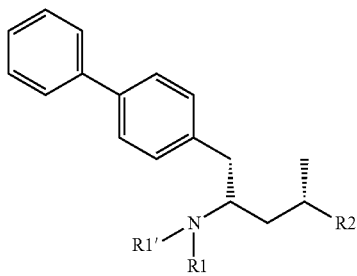

(i)

or salt thereof,
wherein R1 and R1' are independently hydrogen or an amine protecting group, and R2 is a carboxyl group or an ester group, comprising reacting a compound according to formula (ii),

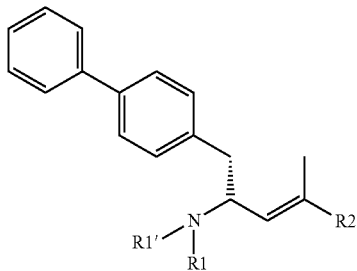

(ii)

or salt thereof,
wherein R1, R1' and R2 are defined as above, with hydrogen in the presence of a transition metal catalyst and a chiral ligand, wherein the transition metal is selected from group 7, 8 or 9 of the periodic table.

Furthermore, the invention relates to products obtainable by said process and to their use in the production of NEP inhibitors. Moreover, the invention relates to the use of transition metal catalyst in the preparation NEP inhibitors or prodrugs thereof, in particular NEP inhibitors comprising a γ-amino-δ-biphenyl-α-methylalkanoic acid, or acid ester, backbone.

Endogenous atrial natriuretic peptides (ANP), also called atrial natriuretic factors (ANF) have diuretic, natriuretic and vasorelaxant functions in mammals. The natural ANF peptides are metabolically inactivated, in particular by a degrading enzyme which has been recognized to correspond to the enzyme neutral endopeptidase (NEP, EC 3.4.24.11), also responsible for e.g. the metabolic inactivation of enkephalins.

In the art biaryl substituted phosphonic acid derivatives are known which are useful as neutral endopeptidase (NEP) inhibitors, e.g. as inhibitors of the ANF-degrading enzyme in mammals, so as to prolong and potentiate the diuretic, natriuretic and vasodilator properties of ANF in mammals by inhibiting the degradation thereof to less active metabolites. NEP inhibitors are thus particularly useful for the treatment of conditions and disorders responsive to the inhibition of neutral endopeptidase (EC 3.4.24.11), particularly cardiovascular disorders such as hypertension, renal insufficiency including edema and salt retention, pulmonary edema and congestive heart failure.

Processes for preparing NEP-inhibitors are known. Those processes usually comprise a hydrogenation step with a palladium catalyst on carbon:

U.S. Pat. No. 5,217,996 describes biaryl substituted 4-amino-butyric acid amide derivatives which are useful as neutral endopeptidase (NEP) inhibitors, e.g. as inhibitors of the ANF-degrading enzyme in mammals. U.S. Pat. No. 5,217,996 discloses N-(3-carboxyl-1-oxopropyl)-(4S)-(p-phenylphenylmethyl)-4-amino-(2R)-methyl butanoic acid ethyl ester as a preferred embodiment. In the preparation of said compound N-t-butoxycarbonyl-(4R)-(p-phenylphenylmethyl)-4-amino-2-methyl-2-butenoic acid ethyl ester 1(ii-a) (4.2 g) is hydrogenated in the presence of palladium on charcoal to give N-t-butoxycarbonyl-(4S)-(p-phenylphenylmethyl)-4-amino-2-methylbutanoic acid ethyl ester as a 80:20 mixture of diastereomers 1(i-a): 1(i-b).

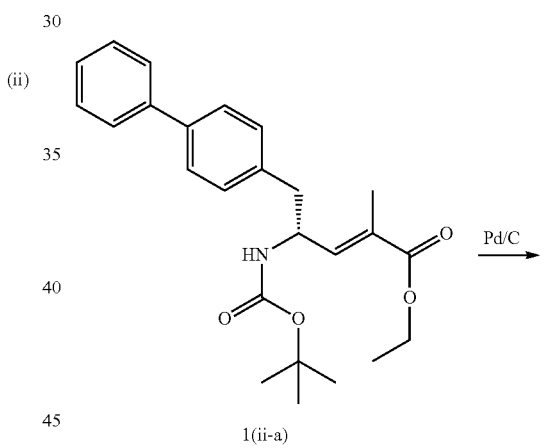

1(ii-a)

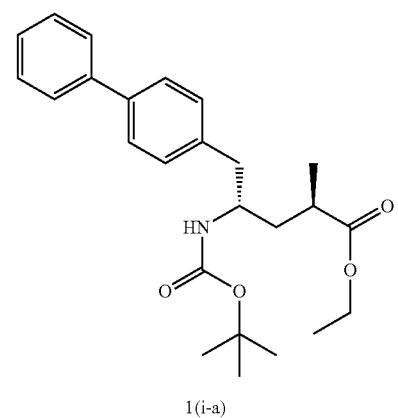

1(i-a)

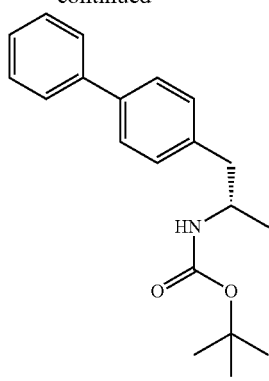

1(i-b)

1(i-a):1(i-b) 80:20

U.S. Pat. No. 5,250,522 describes phosphonomethyl-biaryl substituted amino acid derivatives which show NEP inhibitor activity. A preferred embodiment is (S)-5-(Biphenyl-4-yl)-4-[(dimethylphosphonomethyly)-amino]-2-pentenoic acid ethyl ester. In an intermediate step of the preparation of said NEP inhibitor, (S)-4-(t-Butoxycarbonylamino)-5-(biphenyl-4-yl)-pentenoic acid ethyl ester is hydrogenated with a palladium catalyst on carbon to yield (S)-4-(t-butoxycarbonylamino)-5-(biphenyl-4-yl)-pentanoic acid ethyl ester.

Several dicarboxylic acid dipeptide neutral endopeptidase (NEP) inhibitors are described in G. M. Kasander et al., J. Med. Chem. 1995, 38, 1689-1700, "Dicarboxylic Acid Dipeptide Neutral Endopeptidase Inhibitors". In the preparation of said inhibitors a palladium-catalyzed hydrogenation occurs.

It was an object of the present invention to provide an alternative hydrogenation step in a process for producing NEP inhibitors or prodrugs thereof, in particular it was an object to provide an alternative process for producing compounds according to formula (i), or salts thereof, which can be used as intermediates in the preparation of NEP inhibitors, or prodrugs thereof, in particular NEP inhibitors comprising a γ-amino-δ-biphenyl-α-methylalkanoic acid, or acid ester, backbone.

It was a further object to provide a process in which heterogeneous carriers can be avoided.

It was a still further object to provide a process for producing compounds according to formulae (i-a) and (i-b), or salts thereof, wherein R1, R1' and R2 are defined as above, having a high diastereomeric ratio, preferably more than 88:12.

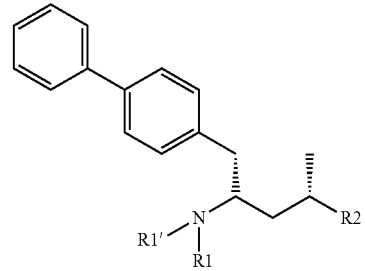

(i-b)

It was an even further object to provide a process for obtaining a high diastereomeric ratio of compounds according to formula (i-a), or salts thereof, to compounds according to formula (i-b), or salts thereof; preferably higher than 88:12; more preferably higher than 90:10. It was also an object to provide a process in which the compounds according to formula (i-b), or salts thereof, can be completely removed and compounds according to formula (i-a), or salts thereof, can be provided in pure form.

It was yet a further object to provide a process for obtaining a diastereomeric ratio of compounds according to formula (i-b), or salts thereof, to compounds according to formula (i-a), or salts thereof, higher than 88:12, preferably more than 90:10. It was also an object to provide a process in which the compounds according to formula (i-a), or salts thereof, can be completely removed and compounds according to formula (i-b), or salts thereof, can be provided in pure form.

It was a still further object to provide a process for producing compounds according to formulae (i-c) and (i-d), or salts thereof, wherein R1, R1' and R2 are defined as above, having a high diastereomeric ratio, preferably more than 88:12.

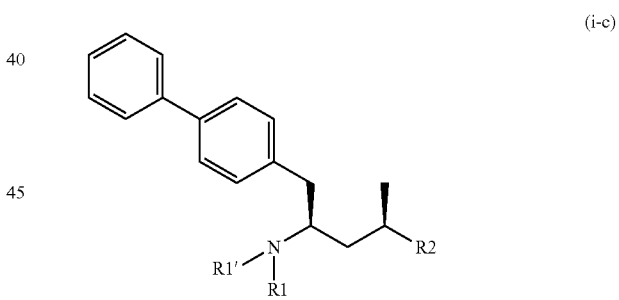

(i-c)

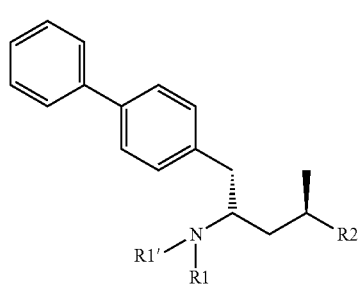

(i-a)

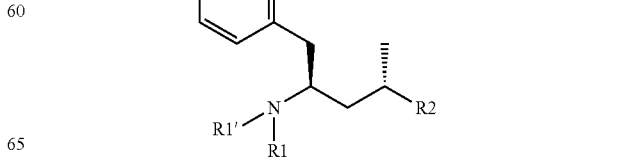

(i-d)

It was an even further object to provide a process for obtaining a diastereomeric ratio of compounds according to formula (i-c), or salts thereof, to compounds according to formula (i-d), or salts thereof, higher than 88:12, preferably more than 90:10. It was also an object to provide a process in which the compounds according to formula (i-c), or salts thereof, can be completely removed and compounds according to formula (i-d), or salts thereof, can be provided in pure form.

It was another object to provide a hydrogenation step in a process for producing NEP inhibitors or prodrugs thereof, in particular NEP inhibitors comprising a γ-amino-δ-biphenyl-α-methylalkanoic acid, or acid ester, backbone. wherein the hydrogenation step preferably has a high yield and preferably leads to products having a high purity degree, preferably products in a diasteromeric ratio higher than 88:12

The objects of the present invention can be achieved by using a specific catalyst and a specific chiral ligand in a hydrogenation step in the production of an NEP inhibitor, in particular a NEP inhibitor comprising a γ-amino-δ-biphenyl-α-methylalkanoic acid, or acid ester, backbone. Preferably, a specific catalyst and a specific chiral ligand are used in a hydrogenation reaction of compounds according to formula (ii), or salts thereof, particularly in a hydrogenation reaction of compounds according to formula (ii-a), or salts thereof,

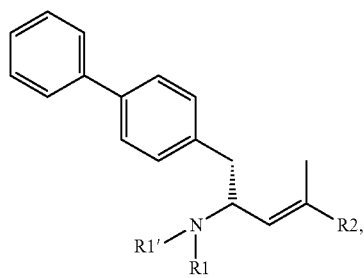

(ii-a)

wherein R1, R1' and R2 are defined as above.

In a further embodiment a specific catalyst and a specific chiral ligand are used in a hydrogenation reaction of compounds according to formula (ii-b),

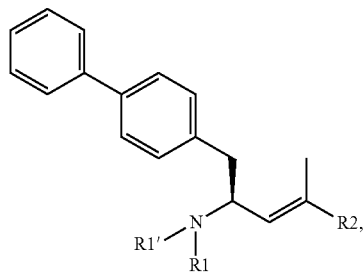

(ii-b)

or salts thereof,
wherein R1, R1' and R2 are defined as above.

Therefore, the subject-matter of the present invention is a process for producing a compound according to formula (i),

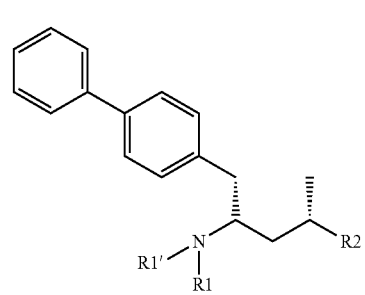

(i)

or salt thereof,
wherein R1 and R1' independently are hydrogen or an amine protecting group and R2 is a carboxyl group or an ester group, comprising reacting a compound according to formula (ii),

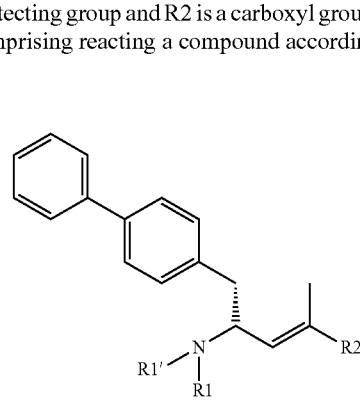

(ii)

or salt thereof,
wherein R1, R1' and R2 are defined as above,
with hydrogen in the presence of a transition metal catalyst and a chiral ligand, wherein the transition metal is selected from group 7, 8 or 9 of the periodic table.

In formulae (i) and (ii) the term "⁓" represents a covalent bond, wherein the stereochemistry of the bond is determined, as either (S) configuration or as (R) configuration of such a chiral centre.

Consequently, compounds according to formula (ii), or salts thereof, are chiral compounds and refer to compounds according to formula (ii-a), or salts thereof, or compounds according to formula (ii-b), or salts thereof.

Accordingly, compounds according to formula (i), or salts thereof, are chiral compounds and refer to compounds according to formulae (i-a), (i-b), (i-c) and (i-d), or salts thereof.

The present invention relates to a process for diastereoselectively hydrogenating a compound of formula (ii) with hydrogen in the presence of a transition metal catalyst and a chiral ligand. The starting material of formula (ii) is chiral, therefore the chirality of both the substrate and the ligand affect the diasteoselectivity in a phenomenon termed "double diastereodifferentiation", ("matched" and "mistmatched" double asymmetric induction).

The degree of facial selectivity observed in the hydrogenation of a chiral compound of formula (ii) in the absence of any other chiral element is the degree of substrate control.

If the facial selectivity of the substrate matches the facial selectivity of the ligand ("matched" double asymmetric induction), the diastereoselectivity of the hydrogenation with hydrogen in the presence of a transition metal catalyst and a chiral ligand would be expected to increase. But, if the facial selectivity of the substrate does not match the facial selectivity of the ligand ("mismatched" double asymmetric induction), high diastereoselectivity would not be expected.

It has been discovered that by employing a process according to the present invention, the hydrogenation of a compound of formula (ii) can be achieved in high diastereoselectivity regardless of the degree of substrate control. Therefore, even when the degree of substrate control is high (for example a diasteromeric ratio of up to 80 to 20), the process of the present invention provides means to obtain any of the possible diasteromeric products with high diastereoselectivity. Thus, advantageously, the present invention allows the stereocontrolled hydrogenation of compounds of formula (ii) regardless of the stereochemistry of the starting compound of formula (ii). The process described herein can thus provide any of (i-a), (i-b), (i-c) and (i-d) with high diastereomeric excess. Accordingly, by employing the process of the present invention, the hydrogenation of a compound of formula (ii-a) can lead to both (i-a) and (i-b) with high diastereomeric excess. Similarly, the hydrogenation of a compound of formula (ii-b) can lead to both (i-c) and (i-d) with high diastereomeric excess.

The compounds of formula (i) have a γ-amino-δ-biphenyl-α-methylalkanoic acid backbone. There are known NEP inhibitors, which have a γ-amino-δ-biphenyl-α-methylalkanoic acid backbone, such as N-(3-carboxy-1-oxopropyl)-(4S)-p-phenylphenylmethyl)-4-amino-(2R)-methylbutanoic acid. Therefore, the present invention provides a novel asymmetric approach towards the preparation of NEP inhibitors. More importantly, the approach proceeds with high stereocontrol.

In formulae (i) and (ii) R1 and R1' are independently hydrogen or an amine protecting group.

It is preferred that R1 is an amine protecting group. It is further preferred that R1' is hydrogen. That means, in a preferred embodiment R1 is one of the below explained preferred amine protecting groups and R1' is hydrogen. Alternatively, R1 and R1' can together form a cyclic ring structure (and thus form a bifunctional cyclic amine protecting group).

The term "amine protecting group" comprises any group which is capable of reversibly protecting the amino functionality. Suitable amine protecting groups are conventionally used in peptide chemistry and are described e.g. in standard reference works such as J. F. W. McOmie, "Protective Groups in Organic Chemistry", Plenum Press, London and New York 1973, in T. W. Greene and P. G. M. Wuts, "Protective Groups in Organic Synthesis", Fourth edition, Wiley, New York 2007, in "The Peptides"; Volume 3 (editors: E. Gross and J. Meienhofer), Academic Press, London and New York 1981, and in "*Methoden der organischen Chemie*" (Methods of Organic Chemistry), Houben Weyl, 4th edition, Volume 15/I, Georg Thieme Verlag, Stuttgart 1974.

Preferred protecting groups comprise, for example, $C_1$-$C_2$-alkyl which is mono-, di- or trisubstituted by phenyl, such as benzyl, (or) benzhydryl or trityl, wherein the phenyl ring is unsubstituted or substituted by one or more, e.g. two or three, residues e.g. those selected from the group consisting of $C_1$-$C_7$-alkyl, hydroxy, $C_1$-$C_7$-alkoxy, $C_2$-$C_8$-alkanoyl-oxy, halogen, nitro, cyano, and $CF_3$; phenyl-C1-C2-alkoxycarbonyl; and allyl or cinnamyl. Especially preferred are benzyloxycarbonyl (Cbz), 9-fluorenylmethyloxycarbonyl (Fmoc), benzyloxymethyl (BOM), pivaloyl-oxy-methyl (POM), trichloroethxoycarbonyl (Troc), 1-adamantyloxycarbonyl (Adoc), but can also be benzyl, cumyl, benzhydryl, trityl, allyl, $C_{1-10}$ alkenyloxy carbonyl, such as alloc (allyloxycarbonyl). The protecting group can also be silyl, like trialklysilyl, especially trimethylsilyl, tert.-butyl-dimethylsilyl, triethylsilyl, triisopropylsilyl, trimethylsilyethoxymethyl (SEM), and can also be sulfonyl, such as methanesulfonyl, trifluoromethanesulfonyl and benzylsulfonyl, or sulfenyl, such as benzenesulfenyl.

R1 and/or R1' can also be a succinimidyl group or an acetal group.

Examples for R1 and/or R1' further include $C_{1-10}$ alkenyloxy carbonyl, $C_{6-10}$aryl-$C_{1-6}$alkyl, and $C_{1-6}$alkyl-carbonyl, $C_{6-10}$aryl-carbonyl, $C_{1-6}$alkoxy-carbonyl, and $C_{6-10}$aryl-$C_{1-6}$alkoxycarbonyl. In a preferred embodiment, R1 is $C_{6-10}$aryl-$C_{1-6}$alkoxycarbonyl, $C_{1-6}$alkoxy-carbonyl, allyloxycarbonyl or $C_{6-10}$aryl-$C_{1-6}$alkyl such as benzyl, t-butoxycarbonyl (BOC).

In a particularly preferred embodiment, R1 is t-butoxycarbonyl (BOC). More preferred is that R1 is t-butoxycarbonyl (BOC) and R1' is hydrogen.

In another particularly preferred embodiment R1 and/or R1' are independently hydrogen or selected from a benzyl group, a succinimdyl group, an acetal group, a silyl group or an oxycarbonyl group.

In yet another particularly preferred embodiment R1 and/or R1' are independently hydrogen or an amine protective group selected from the group consisting of $C_{1-6}$alkyl which is mono-, di- or trisubstituted by $C_{6-10}$aryl, wherein the aryl ring is unsubstituted or substituted by one, two or three, residues selected from the group consisting of $C_{1-7}$alkyl, hydroxy, $C_{1-7}$alkoxy, halogen, nitro, cyano and $CF_3$; $C_{6-10}$aryl-$C_{1-6}$alkyl, cumyl, phenyl-C1-C2-alkoxycarbonyl, allyl, cinnamyl, 9-fluorenylmethyloxycarbonyl (Fmoc), benzyloxymethyl (BOM), pivaloyloxymethyl (POM), trichloroethxoycarbonyl (Troc), 1-adamantyloxycarbonyl (Adoc), $C_{1-10}$alkenyloxycarbonyl, silyl, sulfonyl, sulfenyl, succinimidyl, $C_{2-6}$alkanoyl, $C_{6-10}$aryl-carbonyl, $C_{1-6}$alkoxy-carbonyl and $C_{6-10}$aryl-$C_{1-6}$alkoxycarbonyl.

In formulae (i) and (ii), the term "ester group" comprises any ester of a carboxyl group generally known in the art; for example groups —COOR3, wherein R3 is selected from the group consisting of: $C_{1-6}$alkyl, such as methyl, ethyl or t-butyl, $C_{1-6}$alkoxy$C_{1-6}$alkyl, heterocyclyl, such as tetrahydrofuranyl, $C_{6-10}$aryloxy$C_{1-6}$alkyl, such as benzyloxymethyl (BOM), silyl, such as trimethylsilyl, t-butyldimethylsilyl and t-butyldiphenylsilyl, cinnamyl, allyl, $C_{1-6}$alkyl which is mono-, di- or trisubstituted by halogen, silyl, cyano or $C_{1-6}$aryl, wherein the aryl ring is unsubstituted or substituted by one, two or three, residues selected from the group consisting of $C_{1-7}$alkyl, $C_{1-7}$alkoxy, halogen, nitro, cyano and $CF_3$; or $C_{1-2}$alkyl substituted by 9-fluorenyl.

In a preferred embodiment, R2 is —COOR3, wherein R3 is a $C_{1-6}$alkyl residue. In particular, R3 is an ethyl group.

In a particularly preferred embodiment R2 is COOH.

Furthermore, in a preferred embodiment R1 is t-butoxycarbonyl. In another preferred embodiment R1 is t-butoxycarbonyl. In both preferred embodiments R1' preferably is hydrogen.

The definitions given above for R1, R1' and R2 also apply to formulae (i-a), (i-b), (i-c), (i-d), (ii-a) and (ii-b).

The reaction of the compound according to formula (ii), or salt thereof, with hydrogen is carried out in the presence of a transition metal catalyst, wherein the transition metal is selected from group 7, 8 or 9 of the periodic table. Therefore, the transition metal catalyst comprises, for example, Manganese (Mn), Rhenium (Re), Iron (Fe), Ruthenium (Ru), Osmium (Os), Cobalt (Co), Rhodium (Rh) and/or Iridium (Ir).

In a preferred embodiment, the transition metal catalyst comprises rhodium, iridium or ruthenium. In a more preferred embodiment the transition metal catalyst comprises rhodium or ruthenium. In a particular preferred embodiment the transition metal catalyst comprises ruthenium.

Generally, the transition metal catalyst is an organometallic complex, comprising one or more of the above-mentioned metal atoms and suitable ligands.

Suitable ligands for the organometallic complex generally are σ-donor ligands, σ-donor/π-acceptor ligands or σ,π-donor/π-acceptor ligands. Examples for suitable kind of ligands are among others carbon monoxide, halides, phosphines, alkenyls, alkinyls, aryls and mixtures thereof.

Examples of preferred ligands for the organometallic complex are: norbornadiene (nbd), cyclooctadiene (cod), cymene, in particular p-cymene, and iodide.

The complexes can comprise a single transition metal. In preferred embodiments the complexes can comprise two or more transition metals, optionally comprising a metal-metal bond. In a preferred embodiment two metal atoms are bridged via two halides.

Examples for preferred transition metal catalysts are [RuI$_2$(p-cymene)]$_2$, [Rh(nbd)$_2$BF$_4$] and [Ir(cod)$_2$Cl]$_2$. More preferred are [RuI$_2$(p-cymene)]$_2$ and [Rh(nbd)$_2$BF$_4$].

A particularly preferred transition metal catalyst is [Rh(nbd)$_2$BF$_4$] {=Bis(norbornadiene)rhodium(1) tetrafluoroborate}

Another particularly preferred transition metal catalyst is [RuI$_2$(p-cymene)]$_2$ (=Diiodo(p-cymene)ruthenium(II) dimer):

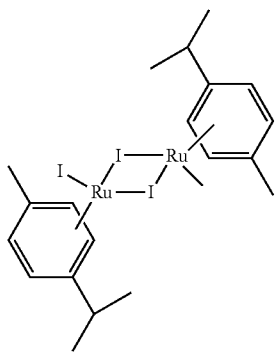

Generally, the term "chiral ligand" comprises any ligand that is suitable to build organometallic complexes and that comprises a chiral centre.

In a preferred embodiment the chiral ligand comprises a chiral phosphine.

It is further preferred that the chiral ligand comprises a chiral ferrocene. It is also preferred that the chiral ligand comprises a ferrocene structure wherein the Cp-ligand of the ferrocene is substituted with a chiral group.

In a preferred embodiment the chiral ligand is selected from Josiphos ligand, Walphos ligand, Taniaphos ligand, Solphos ligand, Mandyphos ligand, Butiphane ligand or mixtures thereof. Josiphos ligands, Walphos ligands, Taniaphos ligands and Mandyphos ligands are of the formulae:

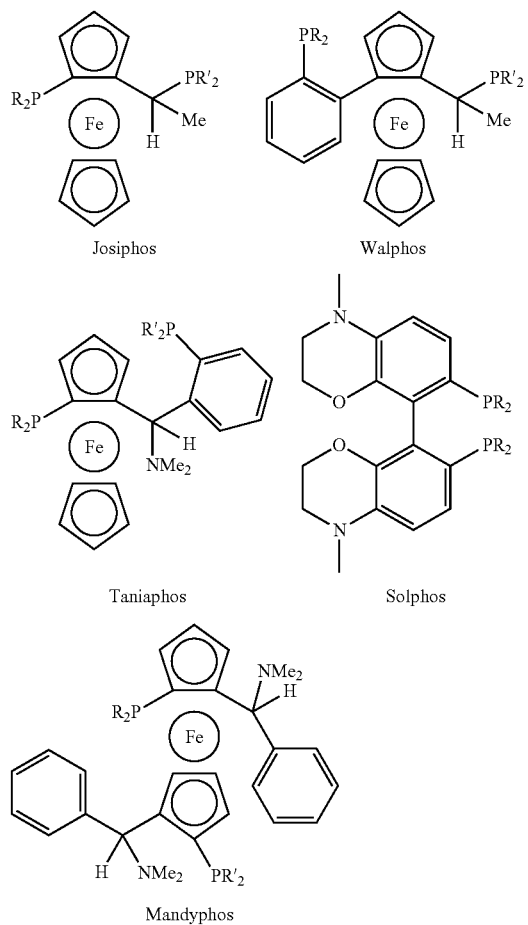

wherein R and R' are as described in WO2006/003196, EP-B1-612758, WO2006/017045, WO2006/117369 and in particular as shown in examples herein.

Examples of suitable chiral ligands are:

Chiral ligands having a Mandyphos structure:

SL-M001-1:

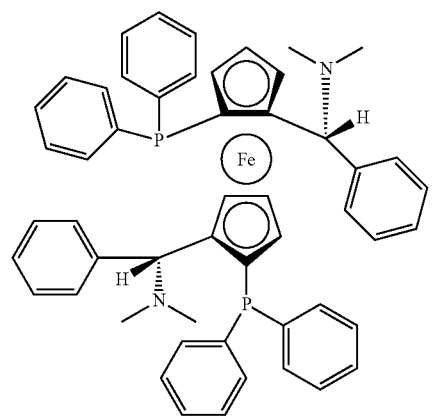

(αR,αR)-2,2'-Bis(α-N,N-dimethylaminophenylmethyl)-(S,S)-1,1'-bis(diphenylphosphino)ferrocene (also known as (R)—(S)—NMe2—PPh2-Mandyphos)

-continued
SL-M004-1:
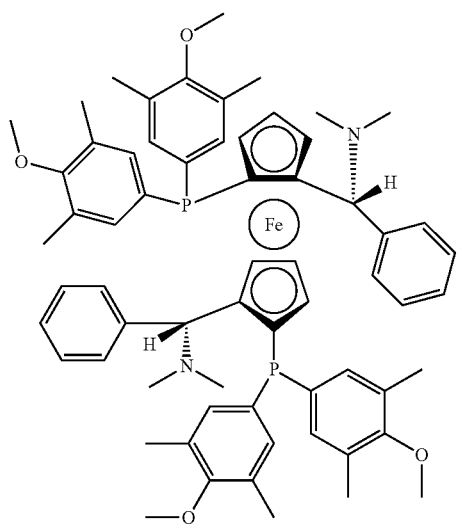
(αR,αR)-2,2'-Bis(α-N,N-dimethylaminophenylmethyl)-(S,S)-1,1'-bis[di(3,5-dimethyl-4-methoxyphenyl)phosphino] ferrocene (also known as
(R)—(S)—NMe2—P(3,5-Me-4-MeOPh)2-Mandyphos)
SL-M004-2:
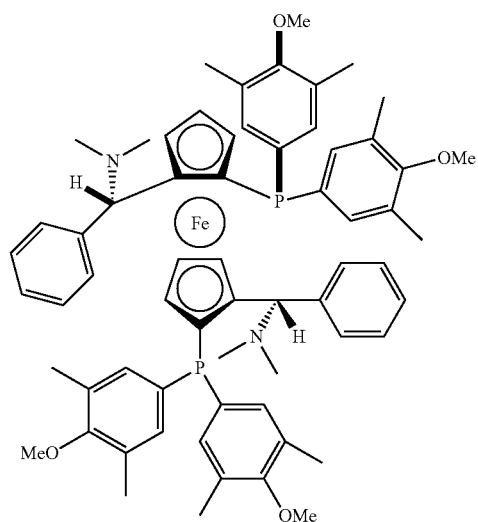
(αS,αS)-2,2'-Bis(α-N,N-dimethylaminophenylmethyl)-(R,R)-1,1'-bis[di(3,5-dimethyl-4-methoxyphenyl)phosphino] ferrocene (also known as
(S)—(R)—NMe2—P(3,5-Me-4-MeOPh)2-Mandyphos)
SL-M002-1:
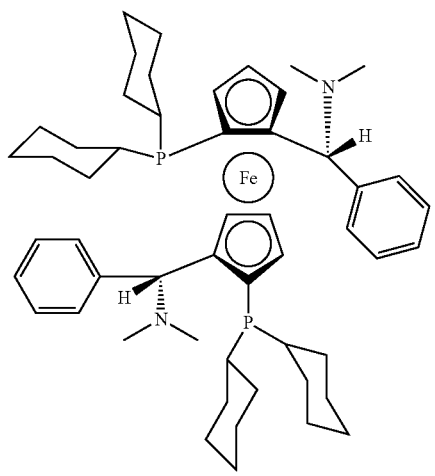
SL-M003-1:
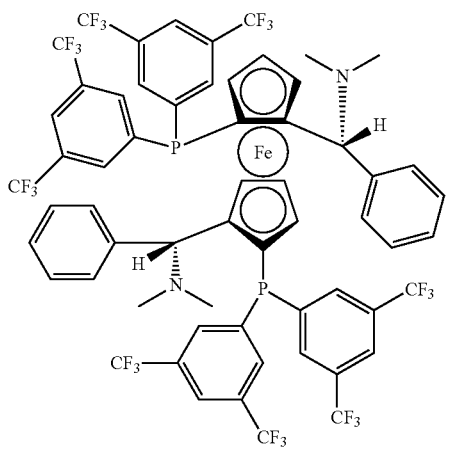
SL-M010-1:
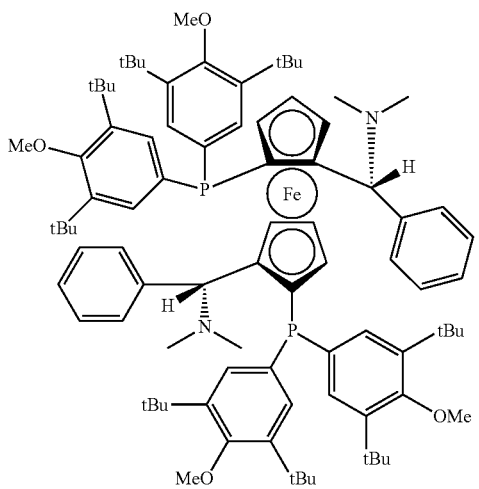

Chiral ligands having a Josiphos structure:
SL-J002-1:
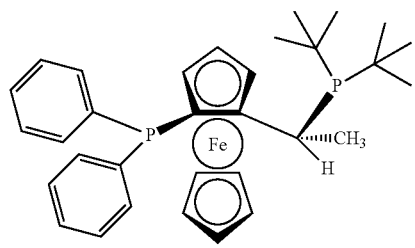
(R)-1-[(S)-2-Dicyclohexylphosphino)-
ferrocenyl]ethyldicyclohexyl-phosohine
SL-J003-1:
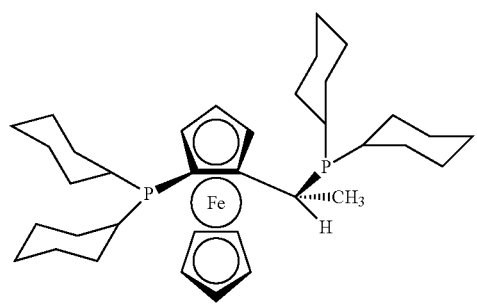
SL-J006-1:
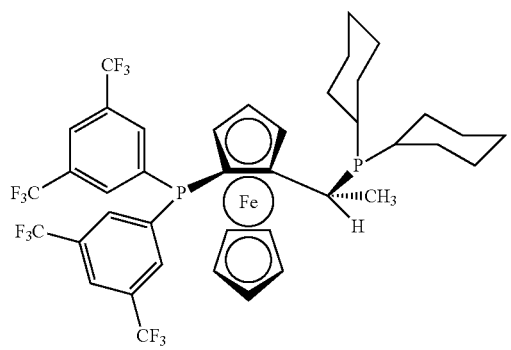
SL-J006-2:
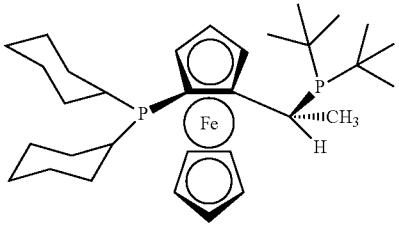
-continued
SL-J009-1:
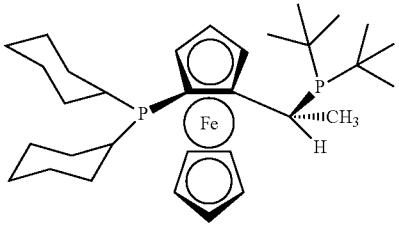
SL-J011-1:
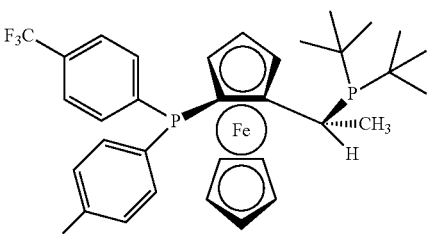
SL-J013-1:
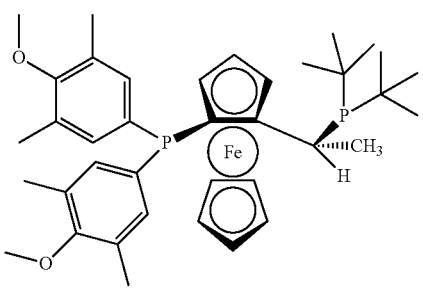
SL-J302-1
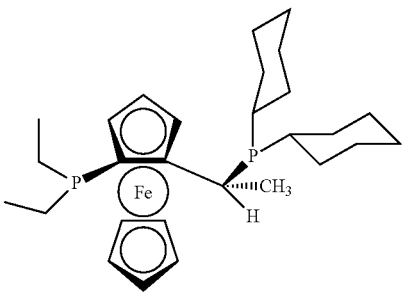
SL-J501-1:
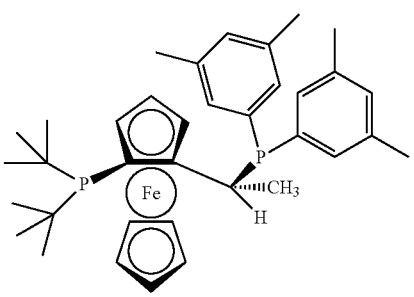

SL-J505-1:
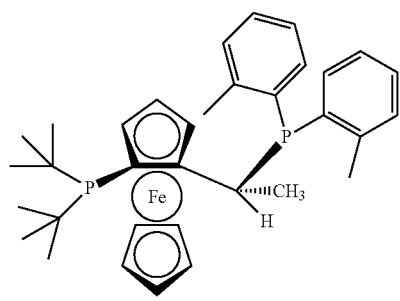
SL-W003-1:
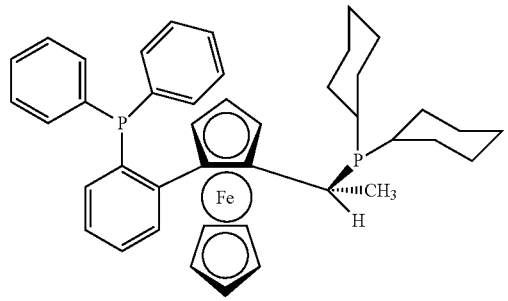
Chiral ligands having a Walphos structure:
SL-W008-1:
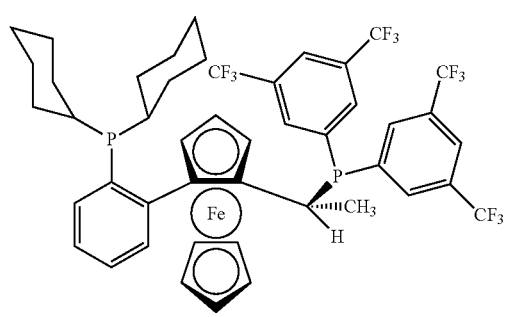
(R)-1-[(R)-2-(2'-Dicyclohexyl-phosphinophenyl)
ferrocenyl]ethyl-di(bis-3,5-trifluoromethyl)phenyl)-phosphine
SL-W005-1:
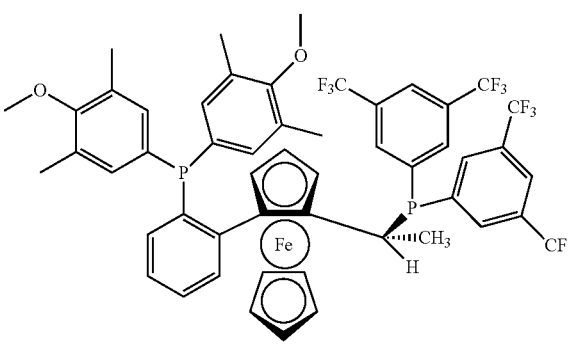
SL-W001-1:
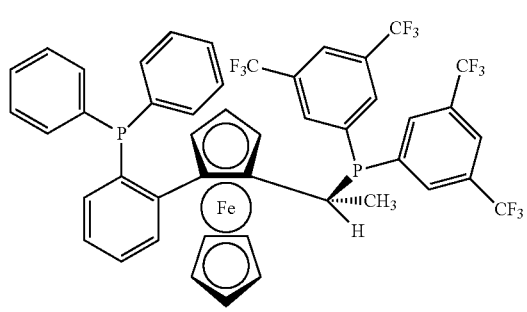
SL-W006-1:
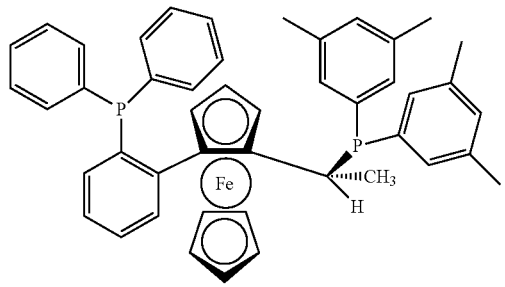
Examples for further suitable chiral ligands are:
SL-W001-2:
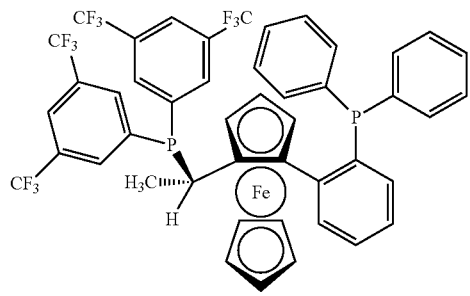
SL-A001-1
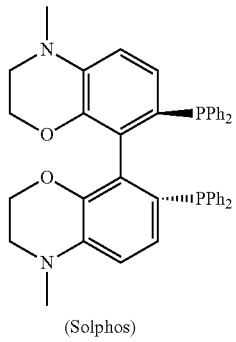
(Solphos)

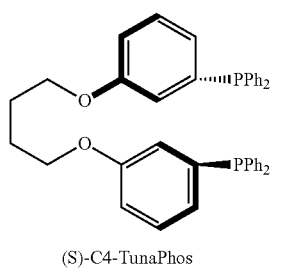
(S)-C4-TunaPhos
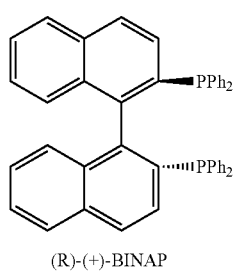
(R)-(+)-BINAP
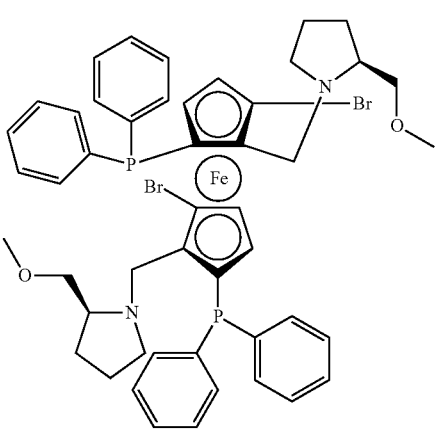
SL-M041-2
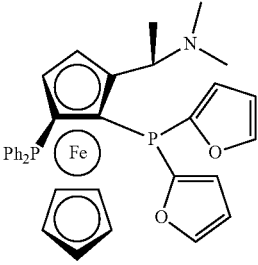
SL-F055-1
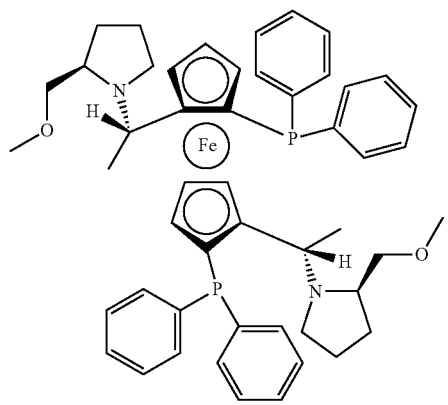
SL-M036-2
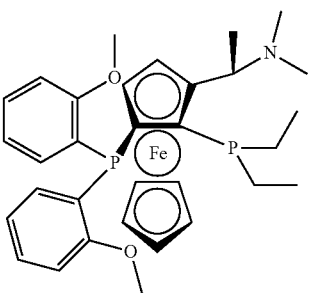
SL-F056-1
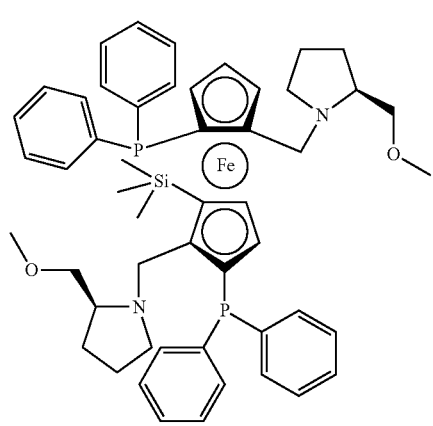
SL-M040-2
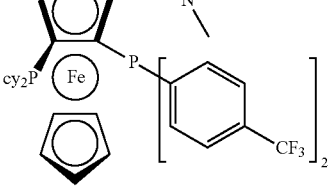
SL-F061-1
SL-F062-1
The preparation of ligand (S)—C4-TunaPhos is described in J. Org. Chem., 2000, 65, 6223 (Example 4). Ligand (R)-(+)-BINAP can be purchased from commercial sources such as Aldrich. All other above-mentioned ligands (Mandyphos, Josiphos, Walphos, Solphos, etc.) are commercially available from Solvias AG (Basel, Switzerland).

Preferred chiral ligands are:
(αR,αR)-2,2'-Bis(α-N,N-dimethylaminophenylmethyl)-(S,S)-1,1'-bis(diphenyl-phosphino)ferrocene (=Mandyphos SL-M001-1),
(αR,αR)-2,2'-Bis(α-N,N-dimethylaminophenylmethyl)-(S,S)-1,1'-bis[di(3,5-dimethyl-4-methoxyphenyl)phosphino]ferrocene (=Mandyphos SL-M004-1),
(αS,αS)-2,2'-Bis(α-N,N-dimethylaminophenylmethyl)-(R,R)-1,1'-bis[di(3,5-dimethyl-4-methoxyphenyl)phosphino]ferrocene (=Mandyphos SL-M004-2),
(αR,αR)-2,2'-bis(α-N,N-dimethylaminophenylmethyl)-(S,S)-1,1'-bis(dicyclohexylphosphino)ferrocene (=SL-M002-1),
(R)—N,N'-Dimethyl-7,7'-bis(diphenylphosphino)-3,3',4,4'-tetrahydro-8,8'-bi-2H-1,4-benzoxazine (=Solphos SL-A001-1),
(R)-1-[(S)-2-Dicyclohexylphosphino)ferrocenyl]-ethyldicyclohexylphosphine (=SL-J003-1),
(R)-1-[(S)-2-Dicyclohexylphosphino)ferrocenyl]ethyldi-tert-butylphosphine (=SL-J009-1),
(S)-1-[(S)-2-(2'-Diphenylphosphinophenyl)ferrocenyl]ethyldi(bis-3,5-trifluoromethylphenyl)phosphine (=SL-W001-2),
(R)-1-[(R)-2-(2'-Diphenylphosphinophenyl)ferrocenyl]-ethyldicyclohexylphosphine (=SL-W003-1),
(R)-1-[(S)-2-Dicyclohexylphosphino)ferrocenyl]ethyldicyclohexylphosphine (=Josiphos SL-J002-1) and/or
(R)-1-[(R)-2-(2'-Dicyclohexylphosphinophenyl)ferrocenyl]ethyldi(bis-(3,5-trifluoro-methyl)phenyl)-phosphine (=Walphos SL-W008-1).

More preferred chiral ligands are:
(αR,αR)-2,2'-Bis(α-N,N-dimethylaminophenylmethyl)-(S,S)-1,1'-bis(diphenyl-phosphino)ferrocene (=Mandyphos SL-M001-1),
(αR,αR)-2,2'-Bis(α-N,N-dimethylaminophenylmethyl)-(S,S)-1,1'-bis[di(3,5-dimethyl-4-methoxyphenyl)phosphino]ferrocene (=Mandyphos SL-M004-1),
(αS,αS)-2,2'-Bis(α-N,N-dimethylaminophenylmethyl)-(R,R)-1,1'-bis[di(3,5-dimethyl-4-methoxyphenyl)phosphino]ferrocene (=Mandyphos SL-M004-2),
(R)-1-[(S)-2-Dicyclohexylphosphino)ferrocenyl]ethyldicyclohexylphosphine (=Josiphos SL-J002-1) and/or
(R)-1-[(R)-2-(2'-Dicyclohexylphosphinophenyl)ferrocenyl]ethyldi(bis-(3,5-trifluoro-methyl)phenyl)-phosphine (=Walphos SL-W008-1).

Even more preferred chiral ligands are:
(αR,αR)-2,2'-Bis(α-N,N-dimethylaminophenylmethyl)-(S,S)-1,1'-bis(diphenyl-phosphino)ferrocene (=Mandyphos SL-M001-1),
(αR,αR)-2,2'-Bis(α-N,N-dimethylaminophenylmethyl)-(S,S)-1,1'-bis[di(3,5-dimethyl-4-methoxyphenyl)phosphino]ferrocene (=Mandyphos SL-M004-1) and/or
(αS,αS)-2,2'-Bis(α-N,N-dimethylaminophenylmethyl)-(R,R)-1,1'-bis[di(3,5-dimethyl-4-methoxyphenyl)phosphino]ferrocene (=Mandyphos SL-M004-2).

Most preferred chiral ligands are:
(αR,αR)-2,2'-Bis(α-N,N-dimethylaminophenylmethyl)-(S,S)-1,1'-bis(diphenyl-phosphino)ferrocene (=Mandyphos SL-M001-1) and/or
(αR,αR)-2,2'-Bis(α-N,N-dimethylaminophenylmethyl)-(S,S)-1,1'-bis[di(3,5-dimethyl-4-methoxyphenyl)phosphino]ferrocene (=Mandyphos SL-M004-1).

Especially preferred as chiral ligand is (αR,αR)-2,2'-Bis(α-N,N-dimethylamino-phenylmethyl)-(S,S)-1,1'-bis[di(3,5-dimethyl-4-methoxyphenyl)phosphino]ferrocene (=Mandyphos SL-M004-1).

In one embodiment, the following combinations of transition metal catalyst and chiral ligand are preferred: rhodium catalyst and a Mandyphos, a Walphos, a Josiphos or a Solphos ligand; more preferably $Rh(nbd)_2BF_4$ and a Mandyphos, a Walphos, a Josiphos or a Solphos ligand; yet more preferably rhodium catalyst and Mandyphos SL-M004-1, Josiphos SL-J003-1, Josiphos SL-J009-1, Walphos SL-W001-2, Walphos SL-W003-1, Walphos SL-W008-1 or Solphos SL-A001-1; even more preferably $Rh(nbd)_2BF_4$ and Mandyphos SL-M004-1, Josiphos SL-J003-1, Josiphos SL-J009-1, Walphos SL-W001-2, Walphos SL-W003-1, Walphos SL-W008-1 or Solphos SL-A001-1.

In another embodiment, the following combinations of transition metal catalyst and chiral ligand are preferred: rhodium catalyst and Walphos SL-W008-1; even more preferably $Rh(nbd)_2BF_4$ and Walphos SL-W008-1. When using these combinations of transition metal catalyst and chiral ligand, by reacting a compound of formula (ii-a), or salt thereof, a composition comprising compounds according to formulae (i-a) and (i-b), or salts thereof, is produced, wherein the molar ratio of (i-a) to (i-b) is at least 88:12.

In another embodiment, the following combinations of transition metal catalyst and chiral ligand are preferred: rhodium catalyst and Mandyphos SL-M004-1, Josiphos SL-J003-1, Josiphos SL-J009-1, Walphos SL-W001-2, Walphos SL-W003-1 or Solphos SL-A001-1; even more preferably $Rh(nbd)_2BF_4$ and Mandyphos SL-M004-1, Josiphos SL-J003-1, Josiphos SL-J009-1, Walphos SL-W001-2, Walphos SL-W003-1 or Solphos SL-A001-1. When using these combinations of transition metal catalyst and chiral ligand, by reacting a compound of formula (ii-a), or salt thereof, a composition comprising compounds according to formulae (i-a) and (i-b), or salts thereof, is produced, wherein the molar ratio of (i-b) to (i-a) is at least 65:35, more preferably at least 73:27.

In another embodiment, the following combinations of transition metal catalyst and chiral ligand are preferred: rhodium catalyst and a Mandyphos or a Walphos ligand; more preferably $[Rh(nbd)_2BF_4]$ and a Mandyphos or a Walphos ligand as well as rhodium catalyst and SL-M004-2 or SL-W008-1; most preferably $[Rh(nbd)_2BF_4]$ and SL-M004-2 or $[Rh(nbd)_2BF_4]$ and SL-W008-1.

In a further embodiment, the following combinations of transition metal catalyst and chiral ligand are preferred: ruthenium catalyst and a Mandyphos or a Josiphos ligand; more preferably $[RuI_2(p\text{-cymene})]_2$ and a Mandyphos or a Josiphos ligand; even more preferably ruthenium catalyst and SL-M001-1, SL-M002-1, SL-M004-1, SL-M004-2 or SL-J002-1; yet more preferably $[RuI_2(p\text{-cymene})]_2$ and SL-M001-1, SL-M002-1, SL-M004-1, SL-M004-2 or SL-J002-1.

In another embodiment the following combinations of transition metal catalyst and chiral ligand are preferred: ruthenium catalyst and Mandyphos SL-M004-2 or SL-M002-1; preferably $[RuI_2(p\text{-cymene})]_2$ and Mandyphos SL-M004-2 or SL-M002-1. When using these combinations of transition metal catalyst and chiral ligand, by reacting a compound of formula (ii-a), or salt thereof, a composition comprising compounds according to formulae (i-a) and (i-b), or salts thereof, is produced, wherein the molar ratio of (i-b) to (i-a) is at least 65:35, more preferably at least 73:27, most preferably at least 94:6.

In still another preferred embodiment the combination of transition metal catalyst and chiral ligand is: ruthenium catalyst and Mandyphos SL-M001-1, Mandyphos SL-M004-1 or Josiphos SL-J002-1; preferably [RuI$_2$(p-cymene)]$_2$ and Mandyphos SL-M001-1, Mandyphos SL-M004-1 or Josiphos SL-J002-1. When using these combinations of transition metal catalyst and chiral ligand, by reacting a compound of formula (ii-a), or salt thereof, a composition comprising compounds according to formulae (i-a) and (i-b), or salts thereof, is produced, wherein the molar ratio of (i-a) to (i-b) is at least 88:12, more preferably at least 98:2.

In yet another preferred embodiment the combination of transition metal catalyst and chiral ligand is: ruthenium catalyst and Mandyphos SL-M004-1; preferably [RuI$_2$(p-cymene)]$_2$ and Mandyphos SL-M004-1. When using these combinations of transition metal catalyst and chiral ligand, by reacting a compound of formula (ii-b), or salt thereof, a composition comprising compounds according to formulae (i-c) and (i-d), or salts thereof, is produced, wherein the molar ratio of (i-c) to (i-d) is at least 88:12, more preferably at least 92:8.

In a still further embodiment, the following combinations of transition metal catalyst and chiral ligand are preferred: ruthenium catalyst and a Mandyphos or a Josiphos ligand; more preferably [RuI$_2$(p-cymene)]$_2$ and a Mandyphos or a Josiphos ligand as well as ruthenium catalyst and SL-M001-1, SL-M004-1 or SL-J002-1; most preferably [RuI$_2$(β-cymene)]$_2$ and SL-M001-1, SL-M004-1 or SL-J002-1.

In particular, the combination [RuI$_2$(p-cymene)]$_2$ and Mandyphos SL-M004-1 is preferred.

The reaction conditions of the process of the present invention are preferably chosen such that the reaction is carried out as a homogenous catalysis. Generally, the term "homogenous catalysis" describes a catalysis where the catalyst is in the same phase (e.g. solid, liquid and gas) as the reactants.

The process of the present invention preferably is not carried out as a heterogeneous catalysis. Generally, the term "heterogeneous catalysis" describes a catalysis where the catalyst is in a different phase to the reactants. Heterogeneous catalysts usually provide a surface for the chemical reaction to take place on.

In the present invention solvents generally known in the art can be used. Preferably, a solvent is used which is able to dissolve the transition metal catalyst and the chiral ligand. Preferably, a polar solvent is used, e.g. a monovalent alcohol. More preferably, the solvent is methanol or ethanol. More preferably, ethanol is used. The amount of solvent employed may be such that the concentration of reactant is in a the range of from 1 to 30% w/v (weight/volume), preferably of from 3 to 25% w/v, more of from 10 to 25% w/v, most preferably of from 20 to 25% w/v.

In a preferred embodiment, the hydrogenation is carried out at a temperature between 0° C. and 80° C., preferably between room temperature and 80° C., more preferably between room temperature and 60° C., even more preferably between room temperature and 45° C., most preferably between room temperature and 35° C.

The hydrogenation usually is carried out at a temperature between 0° C. and 60° C., preferably between 30° C. and 50° C., more preferably between 35° C. and 45° C.

The applied hydrogen pressure usually ranges between 5 bar and 30 bar, preferably between 10 bar to 25 bar, more preferably between 12 bar and bar. The reaction time usually ranges between 1 hour and 25 hours, more preferably between 6 hours and 24 hours, yet more preferably between 5 hours and 20 hours. Most preferably, the reaction time usually ranges from 1 hour to 25 hours, preferably from 5 hours to 20 hours.

In a preferred embodiment, the hydrogen pressure ranges from of 5 bar to bar, preferably from of 5 bar to 20 bar, more preferably from of 10 bar to 20 bar, yet more preferably from of 15 to 20 bar, most preferably the hydrogen pressure is 20 bar.

The amount of transition metal catalyst to substrate (ii), typically employed in the process, may be in the range of from 0.001 to 5% mol, preferably of from 0.001 to 1% mol, more preferably of from 0.003 to 0.3% mol, yet more preferably of from 0.005 to 0.1% mol, most preferably of from 0.01 to 0.05% mol.

Usually, in the inventive process the substrate to catalyst ratio (=S/C ratio) is 100 or higher, preferably 500 or higher, more preferably 1000 or higher. In a preferred embodiment the upper limit of the S/C ratio is 25 000, more preferably 30 000.

In the present invention the term "substrate to catalyst ratio" refers to the molar ratio of starting compounds according to formula (ii), or salts thereof, to "active catalyst" (formed by mixing the transition metal catalyst and the chiral ligand).

Usually, the active catalyst is formed by mixing 0.9 to 1.2, preferably 1.0 to 1.1, more preferably 1.0 to 1.05 mole of chiral ligand with 1.0 mole of transition metal atoms comprised in the transition metal catalyst. For example, if a dimer transition metal catalyst is employed, preferably two moles of chiral ligand are reacted with one mole of transition metal catalyst in order to form the "active catalyst".

The chiral ligand is typically added to the reaction mixture in a solution prepared with the same solvent used for the reaction.

In the process of the present invention preferably a compound according to formula (ii), or salt thereof, in an optically active form is reacted. This means that in the process of the present invention a compound according to formula (ii-a), or salt thereof,

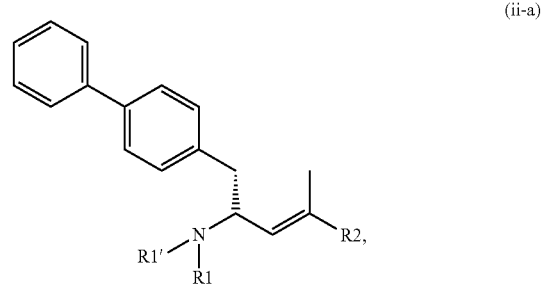

(ii-a)

wherein R1, R1' and R2 are defined as above, or according to formula (ii-b), or salt thereof,

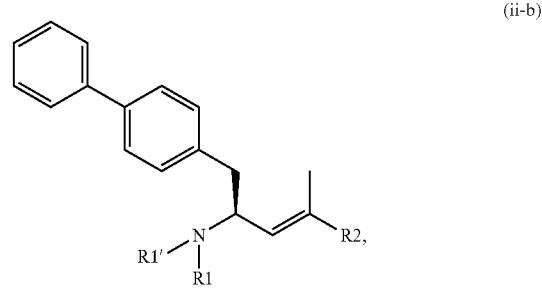

(ii-b)

wherein R1, R1' and R2 are defined as above, can be used as starting compound.

Preferably, compound (ii-a), or salt thereof, is used as starting compound. The synthesis of the starting compound (II), or salt thereof, wherein R1 is BOC, R1' is hydrogen and R2 is COOEt is known in the art.

An example for a possible synthesis of the starting compound (ii-a), or salt thereof, wherein R1 is BOC, R1' is hydrogen and R2 is COOH is given in the reaction scheme below:

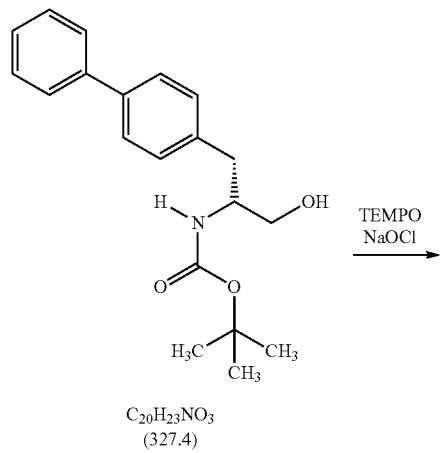

C_{20}H_{23}NO_3
(327.4)

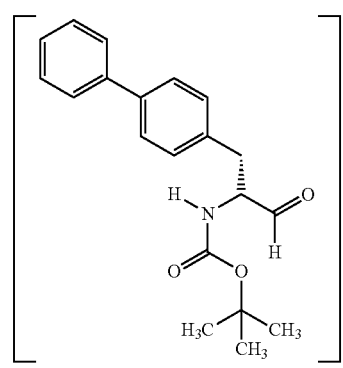

C_{20}H_{23}NO_3
(325.4)

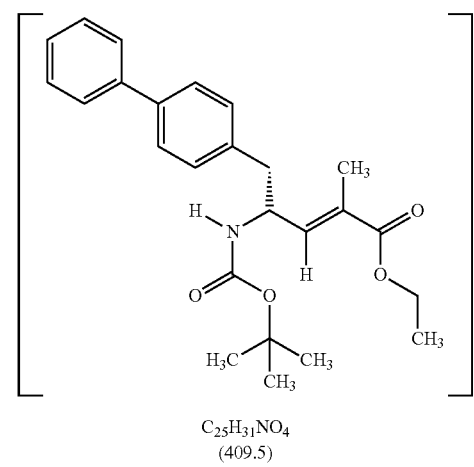

C_{25}H_{31}NO_4
(409.5)

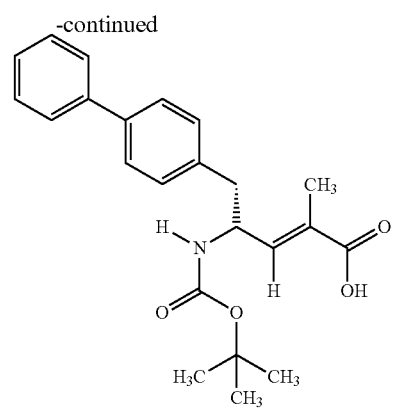

If compound (ii-a), or salt thereof, is used as starting compound, compounds according to formula (i-a)

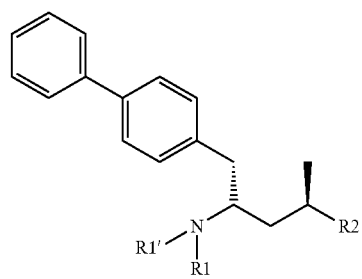

(i-a)

and formula (i-b), or salts thereof,

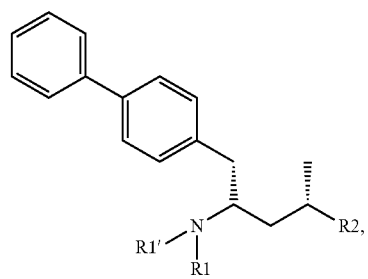

(i-b)

wherein R1, R1' and R2 are defined as above, can be obtained.

If compound (ii-b), or salt thereof, is used as starting compound, compounds according to formula (i-c)

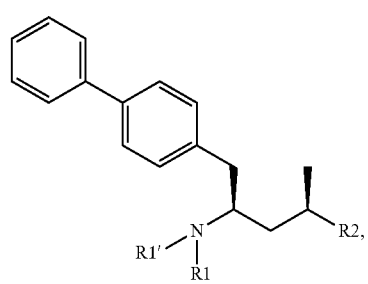

(i-c)

and formula (i-d), or salts thereof,

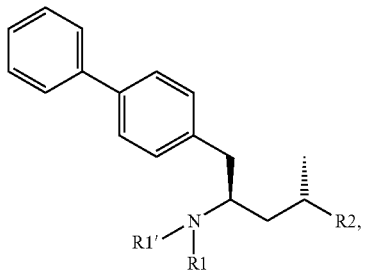

(i-d)

wherein R1, R1' and R2 are defined as above, can be obtained.

The ratio of compounds according to formula (i-a) to (i-b) and (i-c) to (i-d), respectively, or salts thereof, usually depends on the chosen reaction conditions, e.g. on the transition metal catalyst, on the chiral ligand, on the S/C-ratio and/or on the solvent.

Preferably, in the process of the present invention compounds according to formula (i-a), or salts thereof, are produced.

In one preferred embodiment of the process of the present invention a composition comprising compounds according to formulae (i-a) and (i-b), or salts thereof, is produced wherein the molar ratio of compounds according to formula (i-a), or salts thereof, to compounds according to formula (i-b), or salts thereof, is at least 88:12, preferably from 90:10, more preferably from 99 to 1. Most preferably the molar ratio of compounds according to formula (i-a), or salts thereof, to compounds according to formula (i-b), or salts thereof, is at least 88:12, preferably from 90:10 to 99.9:0.1. In a preferred embodiment the process of the present invention provides compounds according to formulae (i-a) and (i-b), or salts thereof, wherein R1 and R1' are independently hydrogen or an amine protecting group and R2 is COOH.

Consequently, a further subject of the present invention is a composition comprising compounds according to formulae (i-a) and (i-b), or salts thereof, wherein the molar ratio (i-a) to (i-b) is at least 88:12, preferably from 90:10, more preferably from 99:1. Most preferably the composition comprises compounds according to formulae (i-a) and (i-b), or salts thereof, wherein the molar ratio (i-a) to (i-b) is at least 88:12, preferably from 90:10 to 99.9:0.1. In a preferred embodiment the composition comprises compounds according to formulae (i-a) and (i-b), or salts thereof, wherein R1 and R1' are independently hydrogen or an amine protecting group and R2 is COOH.

In one preferred embodiment of the process of the present invention a composition comprising compounds according to formulae (i-a) and (i-b), or salts thereof, is produced wherein:
the molar ratio of compounds according to formula (i-a), or salts thereof, to compounds according to formula (i-b), or salts thereof, is at least 88:12, preferably at least 90:10, more preferably at least 99:1,
the combinations of transition metal catalyst and chiral ligand are as described above, preferably: rhodium catalyst and a Mandyphos, a Walphos, a Josiphos or a Solphos ligand; more preferably Rh(nbd)$_2$BF$_4$ and a Mandyphos, a Walphos, a Josiphos or a Solphos ligand; even more preferably rhodium catalyst and a Walphos ligand; yet more preferably rhodium catalyst and Walphos SL-W008-1; most preferably Rh(nbd)$_2$BF$_4$ and Walphos SL-W008-1.

In another preferred embodiment of the process of the present invention a composition comprising compounds according to formulae (i-a) and (i-b), or salts thereof, is produced wherein:
the molar ratio of compounds according to formula (i-a), or salts thereof, to compounds according to formula (i-b), or salts thereof, is at least 88:12, preferably at least 90:10, more preferably at least 99:1,
the combinations of transition metal catalyst and chiral ligand are as described above, preferably: ruthenium catalyst and a Mandyphos or a Josiphos ligand; more preferably [RuI$_2$(p-cymene)]$_2$ and a Mandyphos or a Josiphos ligand; even more preferably ruthenium catalyst and SL-M001-1, SL-M004-1 or SL-J002-1; yet more preferably [RuI$_2$(p-cymene)]$_2$ and SL-M001-1, SL-M004-1 or SL-J002-1, most preferably RuI$_2$(p-cymene)]$_2$ and SL-M001-1 or SL-M004-1.

In one embodiment of the process of the present invention a composition comprising compounds according to formulae (i-a) and (i-b), or salts thereof, is produced wherein:
the molar ratio of compounds according to formula (i-b), or salts thereof, to compounds according to formula (i-a), or salts thereof, is at least 65:35, more preferably at least 73:27, most preferably at least 94:6.

In a preferred embodiment of the process of the present invention a composition comprising compounds according to formulae (i-a) and (i-b), or salts thereof, is produced wherein:
the molar ratio of compounds according to formula (i-b), or salts thereof, to compounds according to formula (i-a), or salts thereof, is at least 65:35, more preferably at least 73:27, most preferably at least 94:6.
the combinations of transition metal catalyst and chiral ligand are as described above, preferably: rhodium catalyst and a Mandyphos, a Walphos, a Josiphos or a Solphos ligand; more preferably Rh(nbd)$_2$BF$_4$ and a Mandyphos, a Walphos, a Josiphos or a Solphos ligand; even more preferably rhodium and Mandyphos SL-M004-1, Josiphos SL-J003-1, Josiphos SL-J009-1, Walphos SL-W001-2, Walphos SL-W003-1, or Solphos SL-A001-1; yet more preferably Rh(nbd)$_2$BF$_4$ and Mandyphos SL-M004-1, Josiphos SL-J003-1, Josiphos SL-J009-1, Walphos SL-W001-2, Walphos SL-W003-1, or Solphos SL-A001-1; most preferably Rh(nbd)$_2$BF$_4$ and Mandyphos SL-M004-1, Walphos SL-W001-2, or Solphos SL-A001-1.

In another preferred embodiment of the process of the present invention a composition comprising compounds according to formulae (i-a) and (i-b), or salts thereof, is produced wherein:
the molar ratio of compounds according to formula (i-b), or salts thereof, to compounds according to formula (i-a), or salts thereof is at least 65:35, more preferably at least 73:27, most preferably at least 94:6,
the combinations of transition metal catalyst and chiral ligand are as described above, preferably: ruthenium catalyst and a Mandyphos or a Josiphos ligand; more preferably [RuI$_2$(p-cymene)]$_2$ and a Mandyphos or a Josiphos ligand; even more preferably ruthenium catalyst and a Mandyphos ligand; yet more preferably ruthenium catalyst and SL-M002-1 or SL-M004-2; still more preferably [RuI$_2$(p-cymene)]$_2$ and SL-M002-1 or SL-M004-2; most preferably [RuI$_2$(p-cymene)]$_2$ and SL-M004-2.

In one embodiment of the process of the present invention a composition comprising compounds according to formulae (i-c) and (i-d), or salts thereof is produced wherein:

the molar ratio of compounds according to formula (i-c), or salts thereof, to compounds according to formula (i-d), or salts thereof is at least 88:12, preferably at least 90:10, more preferably at least 92:8.

In a preferred embodiment of the process of the present invention a composition comprising compounds according to formulae (i-d) and (i-c), or salts thereof, is produced wherein:

the molar ratio of compounds according to formula (i-c), or salts thereof, to compounds according to formula (i-d), or salts thereof is at least 88:12, preferably at least 90:10, more preferably at least 92:8, the combinations of transition metal catalyst and chiral ligand are as described above, preferably: ruthenium catalyst and a Mandyphos or a Josiphos ligand; more preferably [RuI$_2$(p-cymene)]$_2$ and a Mandyphos or a Josiphos ligand; even more preferably ruthenium catalyst and a Mandyphos ligand; yet more preferably ruthenium catalyst and SL-M004-1; most preferably [RuI$_2$(p-cymene)]$_2$ and SL-M004-1.

The process of the present invention can comprise an additional optional step wherein the compounds according to formula (i-a), or salts thereof, are separated from the above-described composition by means of crystallisation.

In a preferred embodiment of the crystallisation step, a composition comprising compounds according to formulae (i-a) and (i-b), or salts thereof, [preferably having a molar ratio of (i-a) to (i-b) of at least 88:12] is dissolved in a suitable polar first solvent, e.g. a monovalent alcohol, preferably ethanol or an ester, preferably isopropylacetate. In a further embodiment, subsequently a suitable less polar second solvent may be added. Preferably, hydrocarbons, e.g. heptane is used as a second solvent. Thus, a preferred system comprising a first and a second solvent is isopropylacetate/heptane.

The crystallisation step yields compounds according to formula (i-a), or salts thereof, in crystalline form. Therefore, the subject-matter of the present invention are compounds, or salts thereof, according to formula (i-a) in crystalline form. Additionally, also compounds, or salts thereof, according to formulae (i-b), (i-c) and (i-d) in crystalline form are subject of the present invention.

In a preferred embodiment the crystalline products of the invention comprise a monoclinic crystal system. Further preferred, the crystalline products of the invention comprise the space group P21. In a preferred embodiment the crystalline products of the invention comprise the following unit cell dimensions, measured at a temperature of 100 K:

---
a = 6-7 Å, preferably 6.8-6.9 Å $\quad \alpha = 90°$
b = 14-15 Å, preferably 14.3-14.5 Å $\quad \beta = 105-106°$, preferably 105.4-105.5°
c = 11-12 Å, preferably 11.3-11.5 Å $\quad \gamma = 90°$.
---

Generally, the same preferred embodiments as discussed above for the inventive process apply to all compounds and compositions of the present invention. This applies in particular to the residues R1, R1' and R2 of formulae (i) and (ii) of the process of the present invention.

Therefore, compounds according to formula (i-a), or salts thereof, in crystalline form are preferred wherein R2 is COOH or RCOOEt, in particular wherein R2 is COOH. Furthermore, R1 preferably is BOC and R1' is preferably hydrogen.

Moreover, the subject-matter of the present invention is, compounds according to formula (i-a)

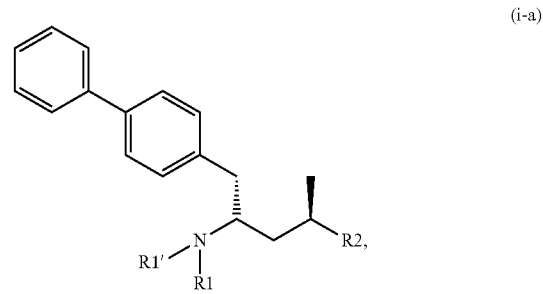

(i-a)

or salts thereof, wherein R1 and R1' are independently hydrogen or an amine protecting group and R2 is a carboxyl group or an ester group, provided that R2 is not COOEt if R1 is BOC and R1' is hydrogen. Preferably, R2 is COOH.

Additionally, the subject-matter of the present invention is compounds according to formulae (i-b), (i-c) and/or (i-d), or salts thereof, wherein R1 and R1' are independently hydrogen or an amine protecting group and R2 is a carboxyl group or an ester group. Preferably, R2 is COOH or COOEt; more preferably R2 is COOH.

The products of the process of the present invention can be used in the synthesis of NEP inhibitors or prodrugs thereof, in particular they can be used in the synthesis of NEP inhibitors comprising a γ-amino-δ-biphenyl-α-methylalkanoic acid, or acid ester, backbone.

The term "NEP inhibitor" describes a compound which inhibits the activity of the enzyme neutral endopeptidase (NEP, EC 3.4.24.11).

The term "prodrug" describes a pharmacological substance which is administered in an inactive (or less active) form. Once administered, the prodrug is metabolised in the body in vivo into the active compound.

Therefore, an embodiment of the process of the present invention comprises one or more additional steps wherein the compound according to formula (i), or salt thereof, is further reacted to obtain a NEP-inhibitor or a prodrug thereof, in particular a NEP-inhibitor or a prodrug thereof comprising a γ-amino-δ-biphenyl-α-methylalkanoic acid, or acid ester, backbone.

In the present invention the terms "NEP-inhibitor" or "NEP-inhibitors prodrug" relates to the substances as such or to salts thereof, preferably pharmaceutically acceptable salts thereof. Examples are sodium, potassium, magnesium, calcium or ammonium salts. Calcium salts are preferred.

Preferably compounds according to formula (i-a), or salts thereof, are further reacted to obtain a NEP-inhibitor or a prodrug thereof, in particular a NEP-inhibitor or a prodrug thereof comprising a γ-amino-δ-biphenyl-α-methylalkanoic acid, or acid ester, backbone. Particularly preferred is a compound according to formula (i-a), or salt thereof, wherein R1 is BOC, R1' is hydrogen and R2 is COOH.

In a preferred embodiment a compound according to formula (i-a), or salt thereof, is further reacted to obtain the NEP inhibitor prodrug N-(3-carboxy-1-oxopropyl)-(4S)-p-phenylphenylmethyl)-4-amino-(2R)-methylbutanoic acid ethyl ester (known in the art as AHU 377) or a salt thereof.

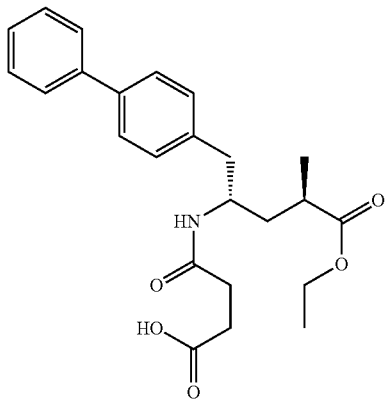

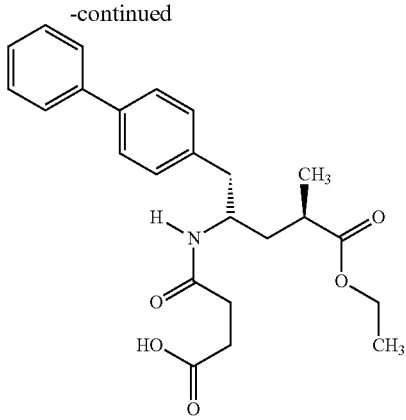

and optionally the following additional steps:

Generally, the present invention comprises any pharmaceutically acceptable salt of N-(3-carboxy-1-oxopropyl)-(4S)-p-phenylphenylmethyl)-4-amino-(2R)-methylbutanoic acid ethyl ester, wherein the calcium salt is preferred.

The NEP inhibitor prodrug N-(3-carboxy-1-oxopropyl)-(4S)-p-phenylphenylmethyl)-4-amino-(2R)-methylbutanoic acid ethyl ester optionally is further reacted to obtain the active NEP inhibitor N-(3-carboxy-1-oxopropyl)-(4S)-p-phenylphenylmethyl)-4-amino-(2R)-methylbutanoic acid.

In a preferred embodiment of the present invention the synthesis of N-(3-carboxy-1-oxopropyl)-(4S)-p-phenylphenylmethyl)-4-amino-(2R)-methylbutanoic acid ethyl ester starts from a compound according to formula (i-a), or salt thereof, preferably, the synthesis starts from the compound of formula (i-a) wherein R1 is preferably BOC, R1' is preferably hydrogen and R2 is preferably COOH. Preferably, said reaction comprises the following steps:

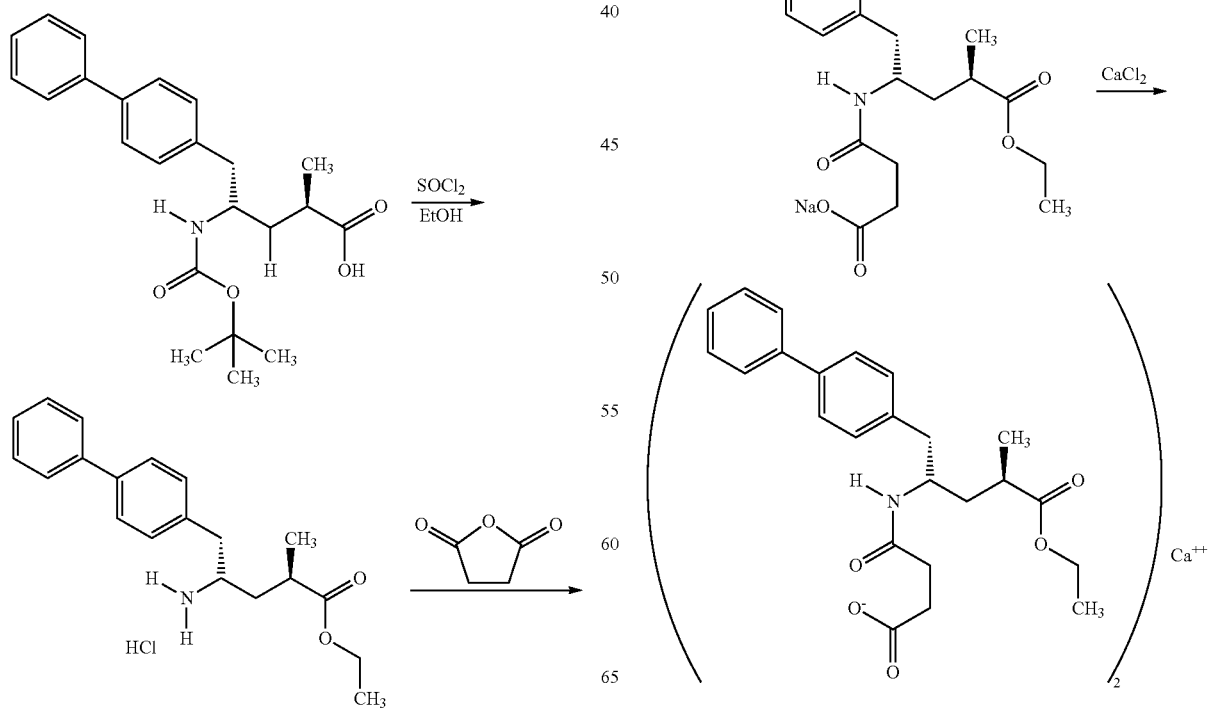

As described above, the inventive process can be used in the synthesis of NEP inhibitors or prodrugs thereof, in particular NEP-inhibitors, or prodrugs thereof, comprising a γ-amino-δ-biphenyl-α-methylalkanoic acid, or acid ester, backbone. Thus, a further subject of the present invention is the use of a transition metal catalyst and a chiral ligand in the synthesis of a NEP inhibitor or a prodrug thereof, in particular a NEP-inhibitor comprising a γ-amino-δ-biphenyl-α-methylalkanoic acid, or acid ester, backbone, wherein the transition metal is selected from group 7, 8 or 9 of the periodic table.

Generally, the same preferred embodiments as discussed above for the inventive process apply to the inventive use. This applies in particular to the disclosure regarding preferred transition metal catalysts, chiral ligands and combinations thereof.

Preferably, the transition metal catalyst and the chiral ligand are used in a hydrogenation step in the synthesis of a NEP inhibitor, in particular a NEP-inhibitor, or prodrug thereof, comprising a γ-amino-δ-biphenyl-α-methylalkanoic acid, or acid ester, backbone. In a preferred embodiment, the hydrogenation step gives two diastereomers having a diastereomeric ratio of at least 88:12, more preferably from 90:10 to 99.9:0.1. In a preferred embodiment the hydrogenation step yields two diastereomers according to formulae (i-a) and (i-b) having a diastereomeric ratio of at least 88:12, more preferably from 90:10 to 99.9:0.1. In another preferred embodiment, the hydrogenation step yields two diastereomers of compounds according to formulae (i-a) and (i-b), or salts thereof, wherein R1 and R1' are as defined above, having a diastereomeric ratio of at least 88:12, preferably at least 90:10, more preferably at least 99:1.

In another preferred embodiment, the transition metal catalyst and the chiral ligand, as defined above, are used in the synthesis of the NEP inhibitor prodrug N-(3-carboxy-1-oxopropyl)-(4S)-p-phenylphenylmethyl)-4-amino-2R-methylbutanoic acid ethyl ester or a salt thereof.

The general definitions used above and below, unless defined differently, have the following meanings:

Alkyl being a radical or part of a radical is a straight or branch (one or, if desired and possible, more times) carbon chain, and is especially $C_1$-$C_7$-alkyl, preferably $C_1$-$C_4$-alkyl.

The term "$C_1$-$C_7$—" defines a moiety with up to and including maximally 7, especially up to and including maximally 4, carbon atoms, said moiety being branched (one or more times) or straight-chained and bound via a terminal or a non-terminal carbon Aryl is, for example $C_{6-10}$aryl, and is, preferably a mono- or polycyclic, especially monocyclic, bicyclic or tricyclic aryl moiety with 6 to 10 carbon atoms.

Unsubstituted or substituted heterocyclyl is a mono- or polycyclic, preferably a mono-, bi- or tricyclic-, most preferably mono-, unsaturated, partially saturated, saturated or aromatic ring system with preferably 3 to 22 (more preferably 3 to 14) ring atoms and with one or more, preferably one to four, heteroatoms independently selected from nitrogen, oxygen, sulfur, S(=O)— or S—(=O)$_2$, and is unsubstituted or substituted by one or more, e.g. up to three, substituents preferably independently selected from the substituents mentioned above for cycloalkyl. When the heterocyclyl is an aromatic ring system, it is also referred to as heteroaryl.

Halo or halogen is preferably fluoro, chloro, bromo or iodo, most preferably fluoro, chloro or bromo.

Halo-alkyl is, for example, halo-$C_1$-$C_7$alkyl and is in particular halo-$C_1$-$C_4$alkyl, such as trifluoromethyl, 1,1,2-trifluoro-2-chloroethyl or chloromethyl. Preferred halo-$C_1$-$C_7$alkyl is trifluoromethyl.

Alkoxy is, for example, $C_1$-$C_7$-alkoxy and is, for example, methoxy, ethoxy, n-propyloxy, isopropyloxy, n-butyloxy, isobutyloxy, sec-butyloxy, tert-butyloxy and also includes corresponding pentyloxy, hexyloxy and heptyloxy radicals. $C_1$-$C_4$alkoxy is preferred.

Alkanoyl is, for example, $C_2$-$C_7$-alkanoyl and is, for example, acetyl [—C(=O)Me], propionyl, butyryl, isobutyryl or pivaloyl. $C_2$-$C_5$-Alkanoyl is preferred, especially acetyl.

Acetyl is —C(=O)$C_1$-$C_7$alkyl, preferably —C(=O)Me.

Alkoxyalkyl may be linear or branched. The alkoxy group preferably comprises 1 to 4 and especially 1 or 2 C atoms, and the alkyl group preferably comprises 1 to 4 C atoms. Examples are methoxymethyl, 2-methoxyethyl, 3-methoxypropyl, 4-methoxybutyl, 5-methoxypentyl, 6-methoxyhexyl, ethoxymethyl, 2-ethoxyethyl, 3-ethoxypropyl, 4-ethoxybutyl, 5-ethoxypentyl, 6-ethoxyhexyl, propyloxymethyl, butyloxymethyl, 2-propyloxyethyl and 2-butyloxyethyl.

Silyl is —SiRR'R", wherein R, R' and R" are independently of each other $C_{1-7}$alkyl, aryl or phenyl-$C_{1-4}$alkyl.

Sulfonyl is $C_1$-$C_7$-alkylsulfonyl, such as methylsulfonyl, (phenyl- or naphthyl)-$C_1$-$C_7$-alkylsulfonyl, such as phenylmethanesulfonyl, [$C_1$-$C_7$-alkyl-, phenyl-, halo-$C_1$-$C_7$-alkyl-, halo, oxo-$C_1$-$C_7$-alkyl-, $C_1$-$C_7$-alkyloxy-, phenyl-$C_1$-$C_7$-alkoxy-, halo-$C_1$-$C_7$-alkyloxy-, phenoxy-, $C_1$-$C_7$-alkanoylamino-, $C_1$-$C_7$-alkylsulfonyl, cyano and/or $C_1$-$C_7$-alkylsulfonyl-]-(mono-, di- or tri-)substituted) (phenyl- or naphthyl)-$C_1$-$C_7$-alkylsulfonyl or (unsubstituted or [$C_1$-$C_7$-alkyl-, phenyl-, halo-lower alkyl-, halo, oxo-$C_1$-$C_7$-alkyl-, $C_1$-$C_7$-alkyloxy-, phenyl-$C_1$-$C_7$-alkoxy-, halo-$C_1$-$C_7$-alkyloxy-, phenoxy-, $C_1$-$C_7$-alkanoylamino-, $C_1$-$C_7$-alkylsulfonyl, cyano and/or $C_1$-$C_7$-alkylsulfonyl-]-(mono-, di- or tri-)substituted) (phenyl- or naphthyl)-sulfonyl wherein if more than one substituent is present the substituents are selected independently from those mentioned. Especially preferred is $C_1$-$C_7$-alkylsulfonyl, such as methylsulfonyl, and (phenyl- or naphthyl)-$C_1$-$C_7$-alkylsulfonyl, such as phenylmethanesulfonyl.

Sulfenyl is (unsubstituted or substituted) $C_{6-10}$aryl-$C_1$-$C_7$-alkylsulfenyl or (unsubstituted or substituted) $C_{6-10}$arylsulfenyl, wherein if more than one substituent is present, e.g. one to four substitutents, the substituents are selected independently from nitro, halo, halo-$C_1$-$C_7$alkyl and $C_1$-$C_7$-alkyloxy.

Alkenyl may be linear or branched alkyl containing a double bond and comprising preferably 2 to 12 C atoms, 2 to 8 C atoms being especially preferred. Particularly preferred is a linear $C_{2-4}$alkenyl. Some examples of alkyl groups are ethyl and the isomers of propyl, butyl, pentyl, hexyl, heptyl, octyl, nonyl, decyl, undecyl, dodecyl, tetradecyl, hexadecyl, octacyl and eicosyl, each of which containing a double bond. Especially preferred is allyl.

Salts are especially pharmaceutically acceptable salts or generally salts of any of the intermediates mentioned herein, where salts are not excluded for chemical reasons the skilled person will readily understand. They can be formed where salt forming groups, such as basic or acidic groups, are present that can exist in dissociated form at least partially, e.g. in a pH range from 4 to 10 in aqueous solutions, or can be isolated especially in solid, especially crystalline, form.

Such salts are formed, for example, as acid addition salts, preferably with organic or inorganic acids, from compounds or any of the intermediates mentioned herein with a basic nitrogen atom (e.g. imino or amino), especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, amino acids, such as glutamic acid or aspartic acid, maleic acid, hydroxymaleic acid, methylmaleic acid, benzoic acid, methane- or ethane-sulfonic acid, ethane-1,2-disulfonic acid, benzenesulfonic acid, 2-naphthalenesulfonic acid, 1,5-naphthalene-disulfonic acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, any of the intermediates mentioned herein may also form internal salts.

For isolation or purification purposes of any of the intermediates mentioned herein it is also possible to use pharmaceutically unacceptable salts, for example picrates or perchlorates.

In view of the close relationship between the compounds and intermediates in free form and in the form of their salts, including those salts that can be used as intermediates, for example in the purification or identification of the compounds or salts thereof, any reference to "compounds", "starting materials" and "intermediates" hereinbefore and hereinafter is to be understood as referring also to one or more salts thereof or a mixture of a corresponding free compound, intermediate or starting material and one or more salts thereof, each of which is intended to include also any solvate or salt of any one or more of these, as appropriate and expedient and if not explicitly mentioned otherwise. Different crystal forms may be obtainable and then are also included.

Where the plural form is used for compounds, starting materials, intermediates, salts, pharmaceutical preparations, diseases, disorders and the like, this is intended to mean one (preferred) or more single compound(s), salt(s), pharmaceutical preparation(s), disease(s), disorder(s) or the like, where the singular or the indefinite article ("a", "an") is used, this is not intended to exclude the plural, but only preferably means "one".

The present invention is illustrated by the following examples.

EXAMPLES

Example 1

(E)-(R)-5-biphenyl-4-yl-4-tert-butoxycarbonylamino-2-methylpent-2-enoic acid

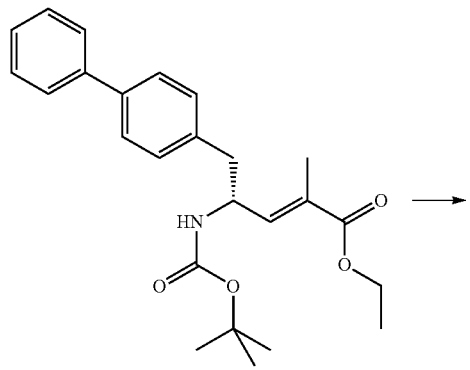

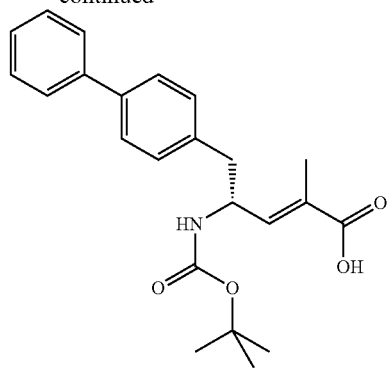

(E)-(R)-5-Biphenyl-4-yl-4-tert-butoxycarbonylamino-2-methylpent-2-enoic acid ethyl ester (CAS#149709-59-1) is hydrolysed using lithium hydroxide in ethanol to yield (E)-(R)-5-biphenyl-4-yl-4-tert-butoxycarbonylamino-2-methylpent-2-enoic acid as a white solid. $\delta_H$ (400 MHz; DMSO) 1.31 (9H, s, (CH$_3$)$_3$), 1.59 (3H, s, 1-CH$_3$), 2.68 (1H, dd, J 6.8, 13.2, 5-H$_A$), 2.86 (1H, m, 5-H$_B$), 4.44 (1H, m, 4-H), 6.51 (1H, d, J 9.2, 3-H), 7.16 (1H, d, J 8.0, NH), 7.26 (2H, d, J 8.0, Ar-ortho-H(Ph)), 7.31 (1H, t, J 7.6, Ar-(Ph)-para-H), 7.40 (2H, t, J 8.0, Ar-(Ph)-meta-H), 7.54 (2H, d, J 8.0, Ar-meta-H (Ph)), 7.60 (2H, d, J 7.6, Ar-(Ph)-ortho-H), 12.26 (1H, s, CO$_2$H); m/z (+ESI) 404 ([MNa]$^+$, 17%), 382 ([MH]$^+$, 2), 326 (10), 264 (100), 167 (13).

Example 2

(2R,4S)-5-biphenyl-4-yl-4-tert-butoxycarbonylamino-2-methylpentanoic acid in crystalline form
[2(i-a)]

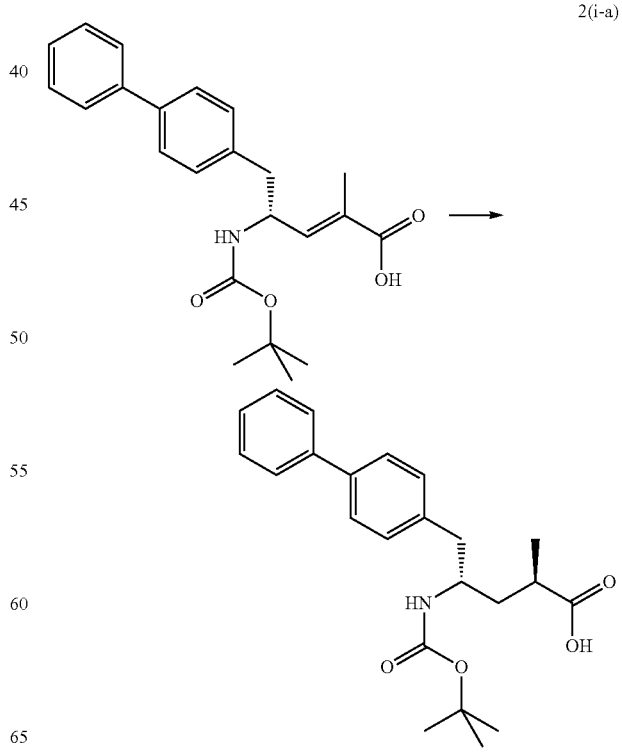

2(i-a)

To a suspension of (E)-(R)-5-biphenyl-4-yl-4-tert-butoxycarbonylamino-2-methylpent-2-enoic acid [2(ii-a)] (200 g, 524.3 mmol) in degassed ethanol (900 ml) at 40° C. a solution of diiodo(p-cymene)ruthenium(II) dimer (0.052 g, 0.0524 mmol) and (αR,αR)-2,2'-bis(α-N,N-dimethylaminophenylmethyl)-(S,S)-1,1'-bis[di(3,5-dimethyl-4-methoxyphenyl)phosphine]ferrocene (=Mandyphos SL-M004-1) (0.116 g, 0.110 mmol) is added in degassed ethanol (100 ml). The solution is degassed using vacuum and a pressure of 20 bar hydrogen applied. The mixture is stirred at 40° C. for 6 h. Vessel is then purged with nitrogen. Ethanol (700 ml) is removed by distillation. Isopropyl acetate (600 ml) is added. Solvent (600 ml) is removed by distillation. Isopropyl acetate (600 ml) is added. Solvent (600 ml) is removed by distillation. Isopropyl acetate (300 ml) is added and the solution is heated to reflux. Heptane fraction (1200 ml) is added and the mixture is cooled to room temperature. The solid is collected by filtration and washed with heptane fraction-isopropyl acetate 2:1 mixture (360 ml). The solid is dried overnight at 50° C. under 1-50 mbar vacuum to afford the title compound as a white/off-white solid [Ratio 2(i-a): 2(i-b) 99:1, as determined by HPLC analysis]. Mpt 146-147° C.; $\delta_H$ (500 MHz; DMSO) 1.07 (3H, d, J 7.0, 1-CH$_3$), 1.34 (9H, s, (CH$_3$)$_3$), 1.38 (1H, m, 3-H$_A$), 1.77 (1H, m, 3-H$_B$), 2.43 (1H, m, 2-H), 2.70 (2H, d, J 7.0, 5-H), 3.69 (1H, m, 4-H), 6.74 (1H, d, J 9.0, NH), 7.27 (2H, d, J 8.0, Ar-ortho-H(Ph)), 7.36 (1H, t, J 7.0, Ar-(Ph)-para-H), 7.46 (2H, t, J 7.5, Ar-(Ph)-meta-H), 7.57 (2H, d, J 8.0, Ar-meta-H(Ph)), 7.64 (2H, d, J 7.5, Ar-(Ph)-ortho-H), 12.01 (1H, s, CO$_2$H); $\delta_C$ (500 MHz, DMSO) 18.1 (1-CH$_3$), 28.3 [(CH$_3$)$_3$], 35.9 (2-C), 37.9 (3-C), 40.7 (5-C), 50.0 (4-C), 77.4 [(C(CH$_3$)$_3$], 126.3, 126.5, 127.2, 128.9, 129.8 (Ar—CH), 137.7 (Ar-ipso-C(Ph)), 138.3 (Ar-para-C(Ph)), 140.1 (Ar-(Ph)-ipso-C), 155.2 (NCO), 177.2 (CO$_2$H); m/z (+ESI) 406 ([MNa]$^+$, 6%), 384 ([MH]$^+$, 31), 328 (100), 284 (19); Found: [MH]$^+$, 384.21691. C$_{23}$H$_{30}$NO$_4$ requires MH 384.21693.

FIG. 1 shows the structure of crystalline (2R,4S)-5-biphenyl-4-yl-4-tert-butoxycarbonylamino-2-methylpentanoic acid measured by x-ray diffraction. The crystals comprise the following unit cell dimensions, measured by 100 K:

| | |
|---|---|
| a = 6.876(2) Å | α = 90° |
| b = 14.399(3) Å | β = 105.458(10)° |
| c = 11.383(3) Å | γ = 90° |

Alternative Procedures (Methods 1 to 5) for the Preparation of 2(i-a):
General Protocol for Methods 1 to 5

To a suspension of (E)-(R)-5-biphenyl-4-yl-4-tert-butoxycarbonylamino-2-methylpent-2-enoic acid [2(ii-a)] (300 mg, 0.79 mmol) in degassed ethanol or methanol (6 ml) at room temperature a solution of transition metal catalyst (S/C ratio 100) and chiral ligand (S/C Ratio 100; 1.05 eq per metal) is added in degassed ethanol or methanol (4 ml). The solution is degassed using vacuum and a pressure of 10 or 15 bar hydrogen is applied for 24 h. The solvent is then removed in vacuo to provide the corresponding product Method 1
Chiral ligand {(R)-1-[(R)-2-(2'-Dicyclohexylphosphinophenyl)-ferrocenyl]ethyldi(bis-(3,5-trifluoromethyl)phenyl)phosphine=SL-W008-1}; Transition metal catalyst {Bis (norbornadiene)rhodium(I) tetrafluoroborate}; MeOH; 15 bar; Ratio 2(i-a): 2(i-b) 89:11 (as determined by HPLC analysis).

Method 2
Chiral ligand {(R)-1-[(R)-2-(2'-Dicyclohexylphosphinophenyl)-ferrocenyl]ethyldi(bis-(3,5-trifluoromethyl)phenyl)phosphine=SL-W008-1}; Transition metal catalyst {Bis (norbornadiene)rhodium(I) tetrafluoroborate}; MeOH; 10 bar; Ratio 2(i-a): 2(i-b) 89:11 (as determined by HPLC analysis).

Method 3
Chiral ligand {(R)-1-[(S)-2-Diphenylphosphino)ferrocenyl]ethyldi-tert-butylphosphine=SL-J002-1}; Transition metal catalyst {diiodo(p-cymene)ruthenium(II) dimer}; EtOH; 15 bar; Ratio 2(i-a): 2(i-b) 90:10 (as determined by HPLC analysis).

Method 4
Chiral ligand {(αR,αR)-2,2'-bis(α-N,N-dimethylaminophenylmethyl)-(S,S)-1,1'-bis[di(3,5-dimethyl-4-methoxyphenyl)phosphine]ferrocene=SL-M004-1}; Transition metal catalyst {diiodo(p-cymene)ruthenium(II) dimer}; EtOH; 15 bar; Ratio 2(i-a): 2(i-b) 99:1 (as determined by HPLC analysis).

Method 5
Chiral ligand {(αR,αR)-2,2'-bis(α-N,N-dimethylaminophenylmethyl)-(S,S)-1,1'-bis[di(3,5-dimethyl-4-methoxyphenyl)phosphino]ferrocene=SL-M001-1}; Transition metal catalyst {diiodo(p-cymene)ruthenium(II) dimer}; EtOH; 15 bar; Ratio 2(i-a): 2(i-b) 98:2 (as determined by HPLC analysis).

(2S,4S)-5-biphenyl-4-yl-4-tert-butoxycarbonylamino-2-methylpentanoic acid [2(i-b)]

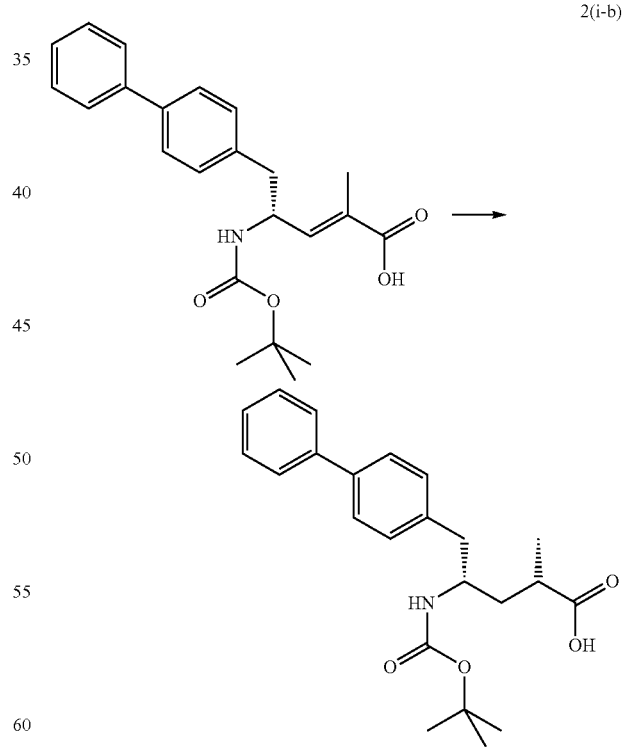

To a suspension of (E)-(R)-5-biphenyl-4-yl-4-tert-butoxycarbonylamino-2-methylpent-2-enoic acid [2(ii-a)] (10 g, 26.1 mmol) in degassed ethanol (90 ml) is added a solution of diiodo(p-cymene)ruthenium(II) dimer (0.156 g, 0.16 mmol) and (αS,αS)-2,2'-bis(α-N,N-dimethylaminophenylmethyl)-

(R,R)-1,1'-bis[di(3,5-dimethyl-4-methoxyphenyl)phosphine]ferrocene (=Mandyphos SL-M004-2) (0.348 g, 0.33 mmol) in degassed ethanol (30 ml) portion wise over the entire reaction time of 5 days. The solution is degassed using vacuum and a pressure of 5.5 bar hydrogen is applied. The mixture is heated to 60° C. and stirred at this temperature for 5 days. The vessel is then purged with nitrogen. The solvent is removed in vacuo. The resulting solid is dissolved in isopropyl acetate (34 ml) and heated to reflux. An heptane fraction (68 ml) is added and the mixture is cooled to room temperature. The solid is collected by filtration and washed with an heptane-isopropyl acetate 2:1 mixture (20 ml). The solid is dried overnight at 50° C. under 1-50 mbar vacuum to afford the title compound [Ratio 2(i-a): 2(i-b) 6:94, as determined by HPLC analysis] as a grey solid. $\delta_H$ (500 MHz; DMSO) 1.06 (3H, d, J 7.0, 1-CH$_3$), 1.32 (9H, s, (CH$_3$)$_3$), 1.42 (1H, m, 3-H$_A$), 1.78 (1H, m, 3-H$_B$), 2.39 (1H, m, 2-H), 2.73 (2H, d, J 7.0, 5-H), 3.73 (1H, m, 4-H), 6.75 (1H, d, J 9.5, NH), 7.29 (2H, d, J 8.0, Ar-ortho-H(Ph)), 7.35 (1H, t, J 7.0, Ar-(Ph)-para-H), 7.46 (2H, t, J 7.5, Ar-(Ph)-meta-H), 7.57 (2H, d, J 8.0, Ar-meta-H(Ph), 7.64 (2H, d, J 7.5, Ar-(Ph)-ortho-H), 12.01 (1H, s, CO$_2$H); $\delta_C$ (500 MHz, DMSO) 16.2 (1-CH$_3$), 28.2 [(CH$_3$)$_3$], 35.7 (2-C), 37.9 (3-C), 40.7 (5-C), 49.2 (4-C), 77.4 [C(CH$_3$)$_3$], 126.3, 126.5, 127.2, 128.9, 129.7 (Ar—CH), 137.8 (Ar-ipso-C(Ph)), 138.4 (Ar-para-C(Ph)), 140.1 (Ar-(Ph)-ipso-C), 155.3 (NCO), 177.6 (CO$_2$H); m/z (+ESI) 406 ([MNa]$^+$, 4%), 384 ([MH]$^+$, 44), 328 (100), 284 (22); Found: [MH]$^+$, 384.21696. C$_{23}$H$_{30}$NO$_4$ requires MH 384.21693.

(2S,4S)-5-biphenyl-4-yl-4-tert-butoxycarbonylamino-2-methylpentanoic acid [2(i-b)] (method 2)

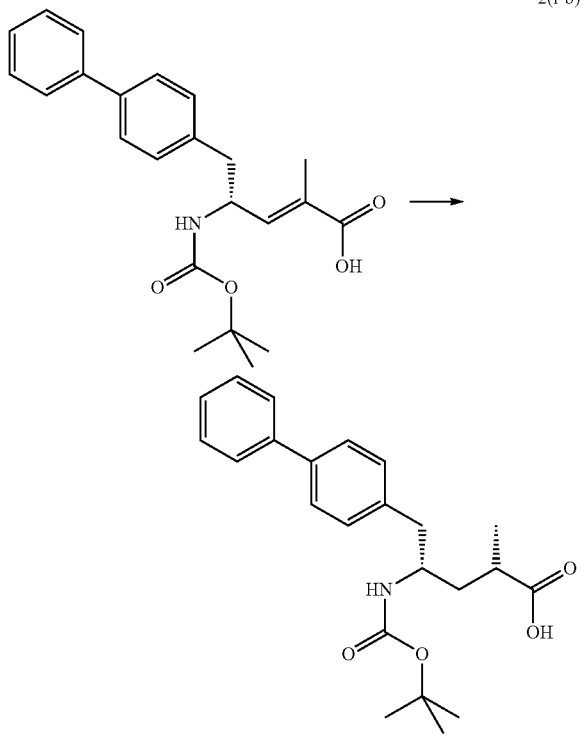

To a suspension of (E)-(R)-5-biphenyl-4-yl-4-tert-butoxycarbonylamino-2-methylpent-2-enoic acid [2(ii-a)] (20 g, 52 mmol) in degassed ethanol (100 ml) is added a solution of diiodo(p-cymene)ruthenium(II) dimer (0.215 g, 0.22 mmol) and (αS,αS)-2,2'-bis(α-N,N-dimethylaminophenylmethyl)-(R,R)-1,1'-bis[di(3,5-dimethyl-4-methoxyphenyl)phosphine]ferrocene (=Mandyphos SL-M004-2) (0.50 g, 0.47 mmol) in degassed ethanol (15 ml). The solution is degassed using vacuum and a pressure of 20 bar hydrogen is applied. The mixture is stirred at 25° C. for 15 h. The vessel is then purged with nitrogen. The solvent is removed in vacuo. The resulting solid is dried overnight at 50° C. under 1-50 mbar vacuum to afford the title compound [Ratio 2(i-a): 2(i-b) 7:93, as determined by HPLC analysis].

Alternative Procedures (Methods 1' to 8') for the Preparation of 2(i-b):

General Protocol for Methods 1' to 8'

To a suspension of (E)-(R)-5-biphenyl-4-yl-4-tert-butoxycarbonylamino-2-methylpent-2-enoic acid [2(ii-a)] (300 mg, 0.79 mmol) in degassed ethanol or methanol (6 ml) at room temperature a solution of transition metal catalyst (S/C ratio 100) and chiral ligand (S/C Ratio 100; 1.05 eq per metal) is added in degassed ethanol or methanol (4 ml). The solution is degassed using vacuum and a pressure of 15 bar hydrogen is applied for 24 h. The solvent is then removed in vacuo to provide the corresponding product.

Method 1':
Chiral ligand {(R)—N,N'-Dimethyl-7,7'-bis(diphenylphosphino)-3,3',4,4'-tetrahydro-8,8'-bi-2H-1,4-benzoxazine=Solphos SL-A001-1}; Transition metal catalyst {Bis(norbornadiene)rhodium(I) tetrafluoroborate}; MeOH; 15 bar; Ratio 2(i-a): 2(i-b) 26:74 (as determined by HPLC analysis).

Method 2':
Chiral ligand {(R)-1-[(S)-2-Dicyclohexyl phosphino)ferrocenyl]-ethyldicyclohexylphosphine=SL-J003-1}; Transition metal catalyst {Bis(norbornadiene)rhodium(I) tetrafluoroborate}; EtOH; 15 bar; Ratio 2(i-a): 2(i-b) 34:66 (as determined by HPLC analysis).

Method 3':
Chiral ligand {(R)-1-[(S)-2-Dicyclohexylphosphino)ferrocenyl]ethyldi-tert-butylphosphine=SL-J009-1}; Transition metal catalyst {Bis(norbornadiene)rhodium(I) tetrafluoroborate}; MeOH; 15 bar; Ratio 2(i-a): 2(i-b) 35:65 (as determined by HPLC analysis).

Method 4':
Chiral ligand {(αR,αR)-2,2'-bis(α-N,N-dimethylaminophenylmethyl)-(S,S)-1,1'-bis[di(3,5-dimethyl-4-methoxyphenyl)phosphine]ferrocene=SL-M 004-1}; Transition metal catalyst {Bis(norbornadiene)rhodium(I) tetrafluoroborate}; MeOH; 15 bar; Ratio 2(i-a): 2(i-b) 27:73 (as determined by HPLC analysis).

Method 5':
Chiral ligand {(S)-1-[(S)-2-(2'-Diphenylphosphinophenyl)ferrocenyl]ethyldi(bis-3,5-trifluoromethylphenyl) phosphine=SL-W001-2}; Transition metal catalyst {Bis(norbornadiene)rhodium(I) tetrafluoroborate}; MeOH; 15 bar; Ratio 2(i-a): 2(i-b) 27:73 (as determined by HPLC analysis).

Method 6':
Chiral ligand {(R)-1-[(R)-2-(2'-Diphenylphosphinophenyl)ferrocenyl]-ethyldicyclohexylphosphine=SL-W003-1}; Transition metal catalyst {Bis(norbornadiene)rhodium(I) tetrafluoroborate}; MeOH; 15 bar; Ratio 2(i-a): 2(i-b) 33:67 (as determined by HPLC analysis).

Method 7':
Chiral ligand {(αR,αR)-2,2'-bis(α-N,N-dimethylaminophenylmethyl)-(S,S)-1,1'-bis(dicyclohexylphosphino) ferrocene=SL-M002-1}; Transition metal catalyst {diiodo(p- cymene)ruthenium(II) dimer}; EtOH; 15 bar; Ratio 2(i-a): 2(i-b) 25:75 (as determined by HPLC analysis).

Method 8':

Chiral ligand {(αS,αS)-2,2'-bis(α-N,N-dimethylaminophenylmethyl)-(R,R)-1,1'-bis[di(3,5-dimethyl-4-methoxyphenyl)phosphine]ferrocene=SL-M004-2}; Transition metal catalyst {diiodo(p-cymene)ruthenium(II) dimer}; EtOH; 15 bar; Ratio 2(i-a): 2(i-b) 6:94 (as determined by HPLC analysis).

Example 3

(2S,4R)-5-biphenyl-4-yl-4-tert-butoxycarbonylamino-2-methylpentanoic acid [3(i-d)]

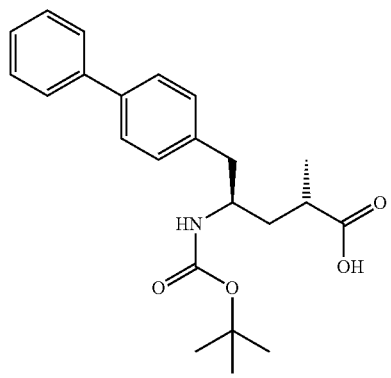

3(i-d)

To a suspension of (E)-(S)-5-biphenyl-4-yl-4-tert-butoxycarbonylamino-2-methylpent-2-enoic acid 3(ii-b) (10 g, 26.2 mmol) and triethylamine (3.6 ml, 26.2 mmol) in isopropyl acetate is added palladium on carbon (1 g, 10% loading). Hydrogen atmosphere is then applied for 5 h. Upon filtering off the catalyst, the solvent is removed in vacuo to give the title compound {3(i-d): 3(i-c) 80:20 ratio; 3(i-d): 3(i-c) 99.9: 0.1 ratio upon recrystallization; as determined by HPLC analysis}.

Recrystallization: 94.5 g of a 80:20 mixture of 3(i-d): 3(i-c) is suspended in isopropyl acetate (190 ml) and heated to reflux to give a solution. Heptane fraction (378 ml) is added and the mixture is cooled to room temperature. The material is collected by filtration and washed with 180 ml Heptane/ Isopropyl acetate (2:1) to give a 91.7:8.3 mixture of 3(i-d): 3(i-c). This mixture is suspended again in isopropyl acetate (280 ml) and heated to reflux. Heptane fraction (560 ml) is added and the mixture cooled to room temperature. The material is collected by filtration and washed with 180 ml Heptane/ Isopropyl acetate (2:1) to give a 99.9:0.1 mixture of 3(i-d): 3(i-c). $\delta_H$ (400 MHz; DMSO) 1.07 (3H, d, J 7.1, 1-CH$_3$), 1.34 (9H, s, (CH$_3$)$_3$), 1.37 (1H, m, 3-H$_A$), 1.76 (1H, m, 3-H$_B$), 2.43 (1H, m, 2-H), 2.69 (2H, d, J 6.8, 5-H), 3.68 (1H, m, 4-H), 6.72 (1H, d, J 8.8, NH), 7.25 (2H, d, J 8.2, Ar-ortho-H(Ph)), 7.34 (1H, m, Ar-(Ph)-para-H), 7.45 (2H, m, Ar-(Ph)-meta-H), 7.57 (2H, d, J 8.2, Ar-meta-H(Ph), 7.64 (2H, d, J 7.9, Ar-(Ph)-ortho-H), 11.97 (1H, s, CO$_2$H); m/z (+ESI) 384 ([MH]$^+$, 66%), 328 (100), 284 (12).

(2R,4R)-5-biphenyl-4-yl-4-tert-butoxycarbonylamino-2-methylpentanoic acid [3(i-c)]

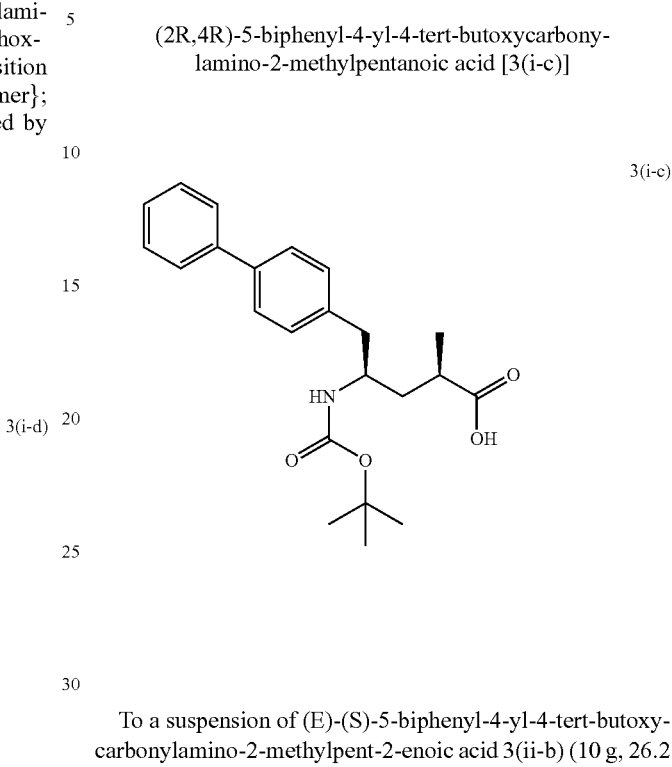

3(i-c)

To a suspension of (E)-(S)-5-biphenyl-4-yl-4-tert-butoxycarbonylamino-2-methylpent-2-enoic acid 3(ii-b) (10 g, 26.2 mmol) in degassed ethanol (80 ml) at 40° C. is added a solution of diiodo(p-cymene)ruthenium(II) dimer (125 mg) and (αR,αR)-2,2'-bis(α-N,N-dimethylaminophenylmethyl)-(S,S)-1,1'-bis[di(3,5-dimethyl-4-methoxyphenyl)phosphine]-ferrocene (290 mg) in degassed ethanol (20 ml). The solution is degassed using vacuum and a pressure of 5.5 bar hydrogen is applied. The mixture is stirred at 40° C. for 24 h. The vessel is then purged with nitrogen. The solution concentrated in vacuo to afford the tittle compound {3(i-d): 3(i-c) 8:92 ratio; as determined by HPLC analysis}.

$\delta_H$ (400 MHz; DMSO) 1.04 (3H, d, J 8.0), 1.32 (9H, s), 1.41 (1H, m), 1.76 (1H, m), 2.36 (1H, m), 2.70 (1H, m), 2.72 (1H, m), 3.70 (1H, m), 6.69 (1H, d, J 8.0), 7.23 (2H, d, J 8.0), 7.32 (1H, m), 7.43 (2H, t, J 8.0), 7.54 (2H, d, J 8.0), 7.60 (2H, d, J 8.0), 12.01 (1H, s); m/z (−ESI) 382 ([M-H]$^-$, 100), 308 (8).

HPLC Conditions:

Column: HP Hypersil, BDS-C 18, 5 μm, 125×4.6 mm. Mobile Phase A (H$_2$O+0.1% trifluoroacetic acid); Mobile Phase B (acetonitrile+0.1% trifluoroacetic acid). Gradient: 0 min (99% A; 1% B); 10 min (100% B); 12 min (100% B). Flow rate: 1 ml min$^{-1}$. Wavelength: 254 nm.

Retention Times:

2R,4S=2(i-a): 11.6 min 2S,4R=3(i-d): 11.6 min 2S,4S=2(i-b): 13.2 min 2R,4R=3(i-c): 13.2 min R=2(ii-a): 13.6 min S=3(ii-b): 13.6 min

The invention claimed is:

1. A process for producing a compound according to formula (i),

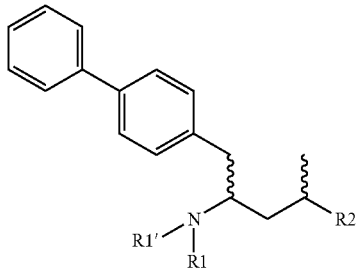

(i)

or salt thereof,
wherein R1 and R1' independently are hydrogen or an amine protecting group and R2 is a carboxyl group or an ester group,
comprising reacting a compound according to formula (ii)

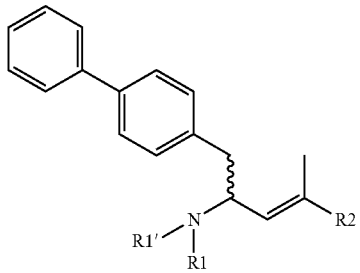

(ii)

or salt thereof,
wherein R1, R1' and R2 are defined as above,
with hydrogen in the presence of a transition metal catalyst and a chiral ligand,
and wherein the transition metal catalyst comprises a dimer ruthenium complex or a dimer rhodium complex and the chiral ligand comprises a chiral phosphine or a chiral ferrocene, wherein the compound according to formula (i) is produced in a diastereomeric ratio of higher than 88:12, and wherein the chiral ligand is a Mandyphos ligand, a Walphos ligand, a Josiphos ligand or a Solphos ligand.

2. A process according to claim 1, wherein the reaction is carried out as a homogenous catalysis.

3. A process according to claim 1, wherein the transition metal catalyst comprises a dimer rhodium complex.

4. A process according to claim to 3, wherein the chiral ligand is Mandyphos SL-M004-1, Josiphos SL-J003-1, Josiphos SL-J009-1, Walphos SL-W001-2, Walphos SL-W003-1, Walphos SL-W008-1 or Solphos SL-A001-1.

5. A process according to claim 4, wherein the transition metal catalyst comprises Rh(nbd)$_2$BF$_4$.

6. A process according to claim 5, wherein the chiral ligand is Walphos SL-W008-1.

7. A process according to claim 1, wherein the transition metal catalyst comprises a dimer ruthenium complex.

8. A process according to claim 7, wherein the transition metal catalyst comprises ruthenium and wherein the chiral ligand is Mandyphos SL-M001-1, Mandyphos SL-M002-1, Mandyphos SL-M004-1 Mandyphos SL-M004-2 or Josiphos SL-J002-1.

9. A process according to claim 8, wherein the transition metal catalyst comprises [RuI$_2$(p-cymene)]$_2$.

10. A process according to claim 9, wherein the chiral ligand is Mandyphos SL-M001-1, Mandyphos SL-M004-1 or Josiphos SL-J002-1.

11. A process according to claim 10, wherein the chiral ligand is Mandyphos SL-M004-1.

12. A process according to claim 9, wherein the chiral ligand is Mandyphos SL-M004-2.

13. A process according to claim 7, wherein the transition metal catalyst comprises [RuI$_2$(p-cymene)]$_2$.

14. A process according to claim 3, wherein the transition metal catalyst comprises Rh(nbd)$_2$BF$_4$.

15. A process according to claim 1, wherein the chiral ligand is a chiral phosphine.

16. A process according claim 1, wherein the chiral ligand is a chiral ferrocene.

17. A process according to claim 1, wherein the chiral ligand is Mandyphos SL-M001-1, Mandyphos SL-M002-1, Mandyphos SL-M004-1 Mandyphos SL-M004-2, Josiphos SL-J002-1, Josiphos SL-J003-1, Josiphos SL-J009-1, Walphos SL-W001-2, Walphos SL-W003-1, Walphos SL-W008-1 or Solphos SL-A001-1.

18. A process according to claim 1, wherein the molar ratio of the compound of formula (ii), or salt thereof, to "active catalyst" (S/C) is 100 or higher.

19. A process according to claim 18, wherein the molar ratio of the compound of formula (ii), or salt thereof, to "active catalyst" (S/C) is from 1 000 to 30 000.

20. A process according to claim 1, wherein a hydrogen pressure of from 5 bar to 25 bar is applied.

21. A process according to claim 1, wherein the compound according to formula (ii) is of formula (ii-a), or salt thereof:

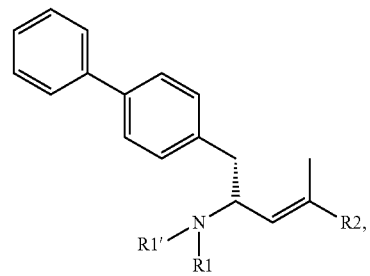

(ii-a)

wherein R1 and R1' and R2 are as defined for the compound of formula (ii).

22. A process according to claim 21, wherein the produced compound according to formula (i) is of formula (i-a):

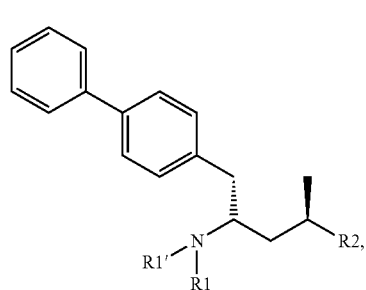

(i-a)

wherein R1, R1' and R2 are as defined for a compound of formula (i).

23. A process according to claim 21, wherein the produced compound according to formula (i) is of formula (i-b):

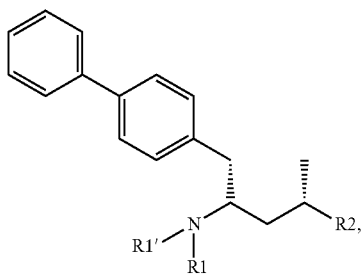

(i-b)

wherein R1, R1' and R2 are as defined for a compound of formula (i).

24. A process according to claim 21, wherein the produced compound according to formula (i) is a composition comprising compounds according to formulae (i-a) and (i-b), or salts thereof,

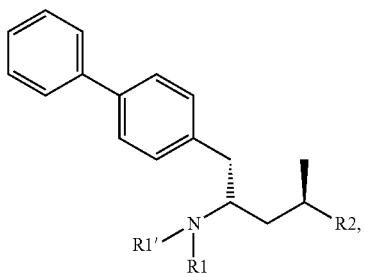

(i-a)

-continued

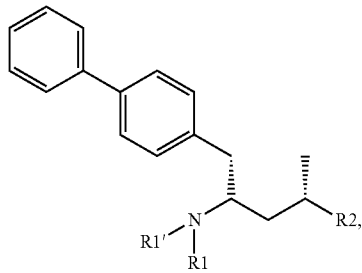

(i-b)

wherein the molar ratio of compounds according to formula (i-a) to compounds according to formula (i-b) is at least 88:12.

25. A process according to claim 24, wherein the transition metal catalyst comprises $[RuI_2(p\text{-cymene})]_2$ and the chiral ligand is Mandyphos SL-M001-1, Mandyphos SL-M004-1, or Josiphos SL-J002-1.

26. A process according to claim 24, wherein the transition metal catalyst comprises $Rh(nbd)_2BF_4$, and the chiral ligand is Walphos SL-W008-1.

27. A process according to claim 24, wherein the compounds according to formula (i-a), or salts thereof, are separated from the composition by means of crystallisation.

28. A process according to claim 27, wherein isopropylacetate and heptane are used as solvents in the crystallization process.

* * * * *